(12) United States Patent
Ayliffe

(10) Patent No.: US 8,616,048 B2
(45) Date of Patent: Dec. 31, 2013

(54) REUSABLE THIN FILM PARTICLE SENSOR

(75) Inventor: Harold E. Ayliffe, Woodinville, WA (US)

(73) Assignee: E I Spectra, LLC, Hailey, ID (US)

(*) Notice: Subject to any disclaimer, the term of this patent is extended or adjusted under 35 U.S.C. 154(b) by 489 days.

(21) Appl. No.: 12/985,536

(22) Filed: Jan. 6, 2011

(65) Prior Publication Data

US 2011/0162439 A1    Jul. 7, 2011

Related U.S. Application Data

(63) Continuation-in-part of application No. 12/381,252, filed on Mar. 10, 2009, now Pat. No. 8,171,778, which is a continuation-in-part of application No. 11/800,167, filed on May 4, 2007, now Pat. No. 7,520,164, application No. 12/985,536, which is a continuation-in-part of application No. 12/378,757, filed on Feb. 19, 2009, now Pat. No. 8,072,603, which is a continuation-in-part of application No. 11/701,711, filed on Feb. 2, 2007, now Pat. No. 7,515,268.

(60) Provisional application No. 60/764,697, filed on Feb. 2, 2006, provisional application No. 61/124,121, filed on Apr. 14, 2008, provisional application No. 61/123,248, filed on Jul. 7, 2008, provisional application No. 60/798,155, filed on May 5, 2006, provisional application No. 60/764,697, filed on Feb. 2, 2006.

(51) Int. Cl.
*G01N 15/06* (2006.01)
*G01N 27/00* (2006.01)

(52) U.S. Cl.
USPC .................................... 73/61.71; 324/71.1

(58) Field of Classification Search
USPC .............................. 73/61.41, 61.71; 324/71.1
See application file for complete search history.

(56) References Cited

U.S. PATENT DOCUMENTS

| | | | |
|---|---|---|---|
| 2,656,508 A | 10/1953 | Colter | |
| 3,910,702 A | 10/1975 | Corli | |
| 4,130,754 A | 12/1978 | Fosslien | |
| 4,164,870 A | 8/1979 | Scordato et al. | |

(Continued)

FOREIGN PATENT DOCUMENTS

WO    WO 02072264 A1 * 9/2002 ............ B01L 3/02

*Primary Examiner* — John Fitzgerald
(74) *Attorney, Agent, or Firm* — Brian C. Trask

(57) ABSTRACT

A microfluidic sensor formed by stacking a plurality of substantially non-electrically conductive layers, typically formed from thin polymer films. Certain layers may carry patterned electrodes that are arranged to permit their connection to an electrical interrogation circuit. Electrodes may be disposed in a 3-dimensional array in the sensor. A fluid path through the sensor includes an orifice sized to promote single-file travel of particles. The orifice may be defined by a tunnel passing through at least one layer. Particles entrained in an electrolytic carrier fluid may be detected, or otherwise characterized, by interrogation circuitry connected to certain embodiments of the sensor. Sensors generally include portions of a fluid path disposed parallel to the layers. Sensors may operate under the Coulter principle, and/or Stokes' shift phenomena. In certain embodiments, the sensor may be carried by a cartridge, which is adapted to couple with an interrogation platform. In any case, coupling desirably places the sensor in-circuit with operable interrogation structure, as well as with a fluid-flow control device. Structure included in a cartridge may provide fluid sample loading, routing, and storage capabilities.

20 Claims, 32 Drawing Sheets

(56) References Cited

U.S. PATENT DOCUMENTS

| | | |
|---|---|---|
| 4,488,814 A | 12/1984 | Johnson |
| 4,873,875 A | 10/1989 | Cork |
| 5,126,022 A | 6/1992 | Soane et al. |
| 5,338,427 A | 8/1994 | Shartle et al. |
| 5,376,878 A | 12/1994 | Fischer |
| 5,459,406 A | 10/1995 | Louge |
| 5,516,564 A | 5/1996 | Root et al. |
| 5,695,092 A | 12/1997 | Schrandt |
| 5,800,690 A | 9/1998 | Chow et al. |
| 5,933,707 A | 8/1999 | Ayliffe et al. |
| 6,045,676 A | 4/2000 | Mathies et al. |
| 6,091,975 A | 7/2000 | Daddona et al. |
| 6,169,394 B1 | 1/2001 | Frazier et al. |
| 6,285,807 B1 | 9/2001 | Walt et al. |
| 6,382,228 B1 | 5/2002 | Cabuz et al. |
| 6,396,584 B1 | 5/2002 | Taguchi et al. |
| 6,426,615 B1 | 7/2002 | Mehta |
| 6,437,551 B1 | 8/2002 | Krulevitch et al. |
| 6,440,725 B1 | 8/2002 | Pourahmadi et al. |
| 6,454,945 B1 | 9/2002 | Weigl et al. |
| 6,488,896 B2 | 12/2002 | Weigl et al. |
| 6,638,482 B1 | 10/2003 | Ackley et al. |
| 6,656,431 B2 | 12/2003 | Holl et al. |
| 6,663,353 B2 | 12/2003 | Lipscomb et al. |
| 6,674,525 B2 | 1/2004 | Bardell et al. |
| 6,703,819 B2 | 3/2004 | Gascoyne et al. |
| 6,794,877 B2 | 9/2004 | Blomberg et al. |
| 7,204,139 B2 | 4/2007 | Takayama |
| 7,223,363 B2 | 5/2007 | McNeely et al. |
| 7,223,371 B2 | 5/2007 | Hayenga et al. |
| 7,235,400 B2 | 6/2007 | Adey |
| 7,332,902 B1 | 2/2008 | Vermeire et al. |
| 7,392,908 B2 | 7/2008 | Frazier |
| 7,410,809 B2 | 8/2008 | Goix et al. |
| 7,417,418 B1 | 8/2008 | Ayliffe |
| 7,515,268 B1 | 4/2009 | Ayliffe et al. |
| 7,520,164 B1 | 4/2009 | Ayliffe |
| 7,579,823 B1 | 8/2009 | Ayliffe |
| 8,171,778 B2 * | 5/2012 | Ayliffe ............ 73/61.71 |
| 2002/0061260 A1 | 5/2002 | Husar |
| 2002/0117517 A1 | 8/2002 | Unger et al. |
| 2002/0149766 A1 | 10/2002 | Bardell et al. |
| 2003/0180965 A1 | 9/2003 | Yobas et al. |
| 2004/0037739 A1 | 2/2004 | McNeely et al. |
| 2004/0151629 A1 | 8/2004 | Pease et al. |
| 2005/0054078 A1 | 3/2005 | Miller et al. |
| 2005/0118705 A1 | 6/2005 | Rabbill et al. |
| 2005/0255600 A1 | 11/2005 | Padmanabhan et al. |
| 2006/0073609 A1 | 4/2006 | Shimizu |

\* cited by examiner

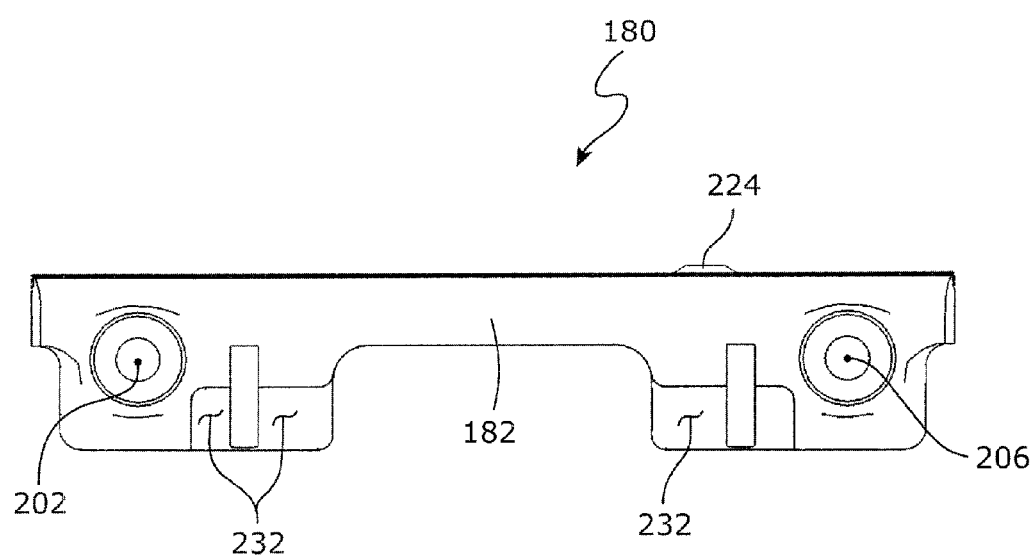
FIG. 10

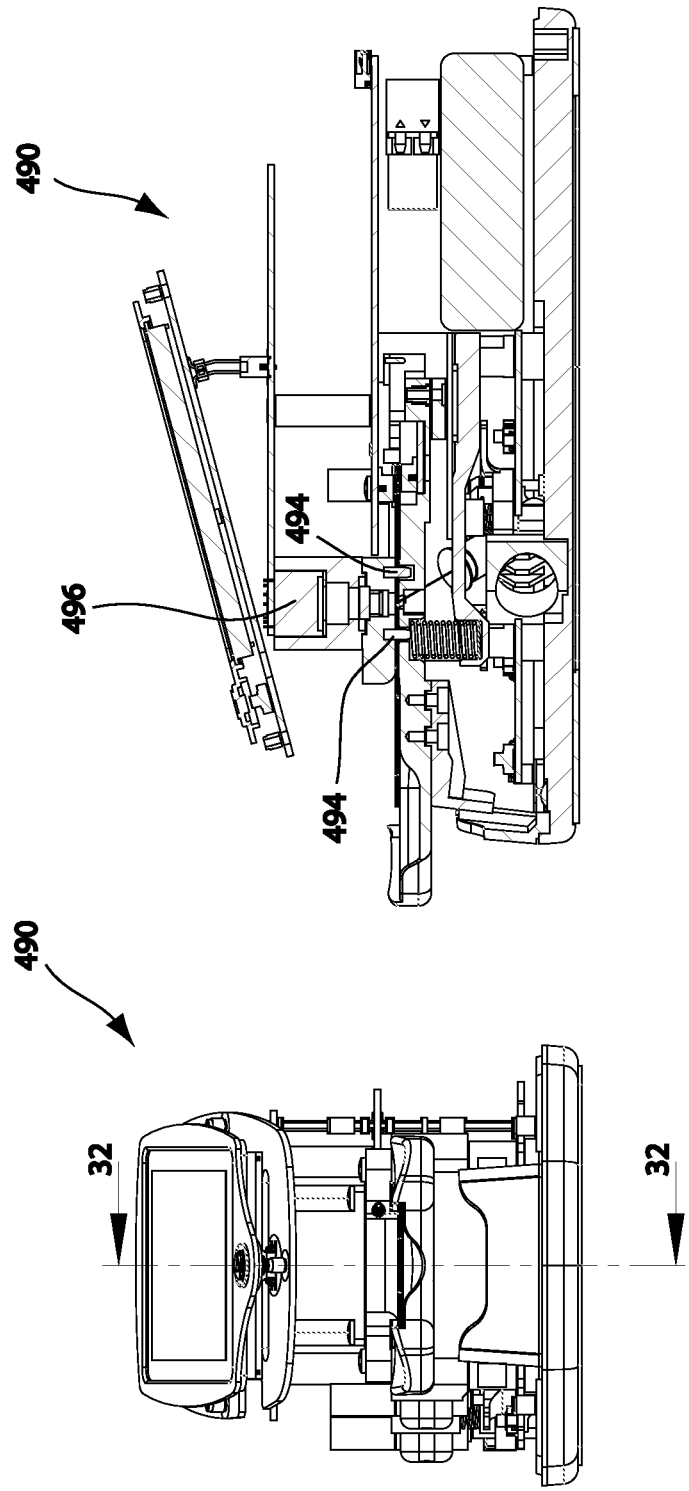

REUSABLE THIN FILM PARTICLE SENSOR

RELATED APPLICATIONS

This application is a continuation-in-part of U.S. utility application Ser. No. 12/381,252, filed Mar. 10, 2009, which is a continuation-in-part of U.S. utility application Ser. No. 11/800,167, filed May 4, 2007, now U.S. Pat. No. 7,520,164, and claims the benefit under 35 U.S.C. 119(e) of the filing date of Provisional Application Ser. No. 60/798,155, filed May 5, 2006, for "THIN FILM PARTICLE SENSOR"; and is a continuation-in-part of U.S. utility application Ser. No. 12/378,757, filed Feb. 19, 2009, which is a continuation-in-part of U.S. utility application Ser. No. 11/701,711, filed Feb. 2, 2007, now U.S. Pat. No. 7,515,268, and claims the benefit under 35 U.S.C. 119(e) of the filing date of Provisional Application Ser. No. 60/764,697, filed Feb. 2, 2006, for "FLUORESCENCE-ACTIVATED CELL DETECTOR"; and is a continuation-in-part of the International Patent Application filed under the Patent Cooperation Treaty, Serial No. PCT/US2009/002172, and claims the benefit under 35 U.S.C. 119 (e) of the filing date of Provisional Application Ser. Nos. 61/123,248, filed Apr. 7, 2008 and 61/124,121, filed Apr. 14, 2008, for "METHOD FOR MANUFACTURING A MICROFLUIDIC SENSOR", the entire disclosures of which are all hereby incorporated by this reference as though set forth in their entirety herein.

BACKGROUND

1. Field of the Invention

This invention relates generally to electrically-based, and/or optically based, sensors for use in detecting, quantifying, qualifying, or otherwise sensing, particles carried by a fluid. It is particularly directed to an improved microfluidic sensor and interrogation structure for such particle sensing application.

2. State of the Art

Pioneering work in particle detection by measuring impedance deviation caused by particles flowing through a small aperture between two containers of electrically conductive fluid is disclosed in U.S. Pat. No. 2,656,508 to W. H, Coulter. Coulter's name is now associated with the principle of particles causing a change in electric impedance as they occlude a portion of the aperture. Since publication of his patent, considerable effort has been devoted to developing and refining sensing devices operating under the Coulter principle.

Relevant U.S. Pat. Nos. include 5,376,878 to Fisher, 6,703, 819 to Gascoyne et al., 6,437,551 to Krulevitch et al., 6,426, 615 to Mehta, 6,169,394 to Frazier et al., 6,454,945 and 6,488,896 to Weigl et al., 6,656,431 to Holl et al., and 6,794, 877 to Blomberg et al. Patent application 2002/117,517 to Unger et al. is also relevant. Each above-referenced document is hereby incorporated by reference, as though set forth herein in their entireties, for their disclosures of relevant technology and structure employed in various sensor arrangements.

Flow cytometry is a well established technique that is used to determine certain physical and chemical properties of microscopic particles by sensing certain optical properties of the particles. Many books and articles are available detailing aspects of this useful investigational tool. For example, operational principles of, and procedures for use of, modern cytometers are set forth in "Practical Flow Cytometry" by Howard M. Shapiro, the contents of which are hereby incorporated by this reference. Flow cytometry is currently used in a wide variety of applications including hematology, immunology, genetics, food science, pharmacology, microbiology, parasitology and oncology.

In flow cytometry, microscopic particles entrained in a carrier fluid are typically arranged in single-file inside a core stream using hydrodynamic focusing. The particles are then individually interrogated by an optical detection system. The interrogation typically includes directing a light beam from a radiation source, such as a laser, transversely across the focused stream of single-file particles. The light beam is scattered by each particle to produce a scatter profile. The scatter profile may be analyzed by measuring the light intensity at both small and larger scatter angles. Certain physical and/or chemical properties of each particle can then be determined from the scatter profile.

It is also known to apply fluorescing markers to selected particles of interest prior to processing such particles in a cytometer. For example, particles such as blood cells can be "tagged" with fluorescent molecules by using conjugated monoclonal antibodies. The wavelength of the radiation source (typically a laser), is matched to the excitation wavelength of the fluorescing molecule marker. The tagged particles fluoresce in the cytometer when excited by the transversely oriented laser beam. The fluorescence given off by the excited particle can be detected by an appropriately configured detector, which is conventionally mounted transverse to the path of the particles in the interrogation portion of the cytometer. Therefore, cells tagged with fluorescing markers can be easily detected for counting, or other data manipulation.

Unfortunately, flow cytometers are undesirably complex and expensive pieces of equipment. Care must be taken to ensure the machine is set up correctly, and properly calibrated. It would be an advance to provide a robust, inexpensive apparatus that can be used to promote single-file particle travel through an optically based interrogation zone to promote rapid processing of a plurality of different particle-bearing fluid samples.

While considerable progress has been made in sensor technology, a need remains for sensors adapted to interrogate particles that are entrained in a conductive fluid, which are low in cost, permit enhanced sample manipulation, and/or ensure accurate selection of a sample volume. It would be an improvement to provide a sensitive and accurate sensor embodied on a cartridge that is sufficiently robust as to permit its use to serially interrogate a plurality of samples. It would be another improvement to provide such a cartridge structured to permit interrogation of a sample having a pre-defined volume. Still further improvements would provide verification of sample presence at one or more desired position in the sensor, verify sensor functionality (or health), and permit estimation of the flow rate and/or volumetric particle count of a fluid sample.

BRIEF SUMMARY OF THE INVENTION

This invention provides devices structured as microfluidic sensors including a multi-layer thin film sandwich that defines a fluid flow path through an interrogation zone, and methods of use and manufacture of those devices. A preferred microfluidic sensor includes a plurality of stacked thin film substantially planar layers forming a cassette providing structure defining a fluid path disposed inside the sensor. An exemplary path includes a first, second, and third portion. The first and third portions are disposed parallel to, and within, the layers. The second portion is provided by a tunnel passing through an interrogation layer. Desirably, a constriction in the tunnel is sized to urge particles entrained in a carrier fluid into substantially single-file travel through a particle interrogation zone. The second and third portions are disposed on opposite sides of the particle interrogation zone.

One preferred cassette is structured for insertion into an interrogation device at a first optical interrogation orientation to permit running a first test, then to permit withdrawal and rotation of the cassette to a second optical interrogation orientation that is different from the first orientation for reinsertion of the cassette to permit running a second test. In certain cases, a cassette may be structured for insertion into an interrogation device at a first electrical connection orientation to permit running a first test, then to permit withdrawal and rotation of the cassette to a second electrical connection orientation that is different from the first orientation for reinsertion of the cassette to permit running a second test.

Certain layers of an alternative cassette carry one or more electrode to dispose a plurality of electrodes in a 3-dimensional array in space. One preferred such sensor includes a first stimulated electrode disposed for contact with fluid in the first portion; a second stimulated electrode disposed for contact with fluid in the third portion; a first interrogation electrode disposed for contact with fluid between the first stimulated electrode and the second stimulated electrode; and a first trigger electrode arrangement operable to indicate a stop signal based upon detection of a fluid boundary. An operable first trigger electrode arrangement includes a dedicated electrode disposed upstream of the second portion.

Certain sensors include a second trigger electrode arrangement operable to indicate a start signal based upon detection of a fluid boundary. One such start trigger includes a dedicated electrode disposed downstream of said second portion and spaced apart from said first trigger electrode arrangement by a length of lumen defining a known volume. Some sensors may also include a third trigger electrode arrangement operable to indicate a stop signal based upon detection of a fluid boundary. An operable third trigger electrode arrangement includes a dedicated electrode disposed downstream of the second portion and spaced apart from the second trigger electrode arrangement by a length of lumen defining a known volume.

Desirably, a waste reservoir is associated with the fluid path and is structured to receive a plurality of individual and serially interrogated fluid samples. Preferred arrangements include means to detect a level of fluid in the reservoir. Sometimes, the waste reservoir is carried by the sensor. Other times, the waste reservoir is associated with an interrogation device.

Currently preferred sensors include alignment hole structure disposed relative to the second portion effective to facilitate precision orienting the second portion of an optically-based testing cassette when the alignment hole structure is installed in registration with alignment pin structure of a cooperatingly structured interrogation device. One workable alignment hole structure includes a first aperture structured to define an X-Y position of a cassette at an installed position in, and with respect to, a cooperatingly structured interrogation device. The alignment structure may further include a second aperture structured to interact with cooperating structure of the interrogation device to enforce substantially only a rotational aspect of the cassette with respect to the X-Y position.

The invention may be embodied in a method for interrogating particles entrained in a carrier fluid. One such method includes providing a microfluidic test cassette; loading a first fluid sample into the cassette; installing the cassette in operable registration, at a first orientation, with an interrogation device; urging flow of the first fluid sample through the cassette while using the interrogation device to interrogate a portion of the first sample; removing the cassette from the interrogation device; loading a second fluid sample into the cassette; re-installing the cassette in operable registration, at a second orientation, with the interrogation device; and urging flow of the second fluid sample through the cassette while using the interrogation device to interrogate a portion of the second sample.

An alternative method for interrogating particles entrained in a carrier fluid includes providing a microfluidic test cassette; interrogating a plurality of fluid samples in series; and electrically monitoring a health-indicating parameter of the cassette between at least two of the samples. In certain cases, the method may include monitoring the level of fluid in a waste fluid reservoir.

A preferred microfluidic test cassette includes a plurality of stacked thin film substantially planar layers forming a cassette providing structure defining a fluid path disposed inside said sensor. In general, the path includes first, second, and third portions. A workable first portion is disposed parallel to, and within, the layers. A workable second portion is provided by a tunnel passing through an interrogation layer, a constriction in the tunnel being sized to urge particles entrained in a carrier fluid into substantially single-file travel through a particle interrogation zone. A workable third portion is disposed parallel to, and within, the layers. Also, the first portion and the third portion of the preferred cassette are disposed on opposite sides of the particle interrogation zone. Certain cassettes may include layers carrying one or more electrode to dispose a plurality of electrodes in a 3-dimensional array in space. An exemplary such cassette includes a first stimulated electrode disposed for contact with fluid in the first portion; a second stimulated electrode disposed for contact with fluid in the third portion; and a first interrogation electrode disposed for contact with fluid between the first stimulated electrode and the second stimulated electrode.

A workable method may include flushing the fluid path with a cleaning fluid during an interval between the interrogation of at least two of the fluid samples. A workable method may include accumulating fluid samples inside a container carried by the cassette, or otherwise associated with an interrogation device.

The invention may also be embodied in a method for manufacturing a multi-layer microfluidic sensor structured as described above. Manufacturing steps may include forming a first fluid-flow channel in a first layer of thin film, the first fluid-flow channel being configured to permit fluid flow in a direction generally parallel to the first layer; forming a second fluid-flow channel passing through a second layer of thin film to create an interrogation layer, the second fluid-flow channel being sized to urge single-file travel therethrough of particles entrained in a carrier fluid; forming a third fluid-flow channel in a third layer of thin film, the third fluid-flow channel being configured to permit fluid flow in a direction generally parallel to the third layer. The first, second, and third fluid-flow channel are typically configured as individual portions of a first lumen extending through the sensor.

The manufacturing method may further include the step of forming a plurality of alignment holes in penetration through the interrogation layer and disposed with sufficient precision relative to the second fluid-flow channel such that installation of two of the alignment holes in registration with respective locating pins of a cooperatingly structured interrogation device is effective to dispose the second fluid-flow channel at an interrogation location of the interrogation device within an accuracy of about 50 µm.

A workable manufacturing method may also include the step of forming a fourth fluid-flow channel in the first layer of thin film, the fourth fluid-flow channel being configured to permit fluid flow in a direction generally parallel to the first layer, and forming a fifth fluid-flow channel passing through the second layer of thin film, the fifth fluid-flow channel being sized to urge single-file travel therethrough of particles entrained in a carrier fluid. The method may also include forming a sixth fluid-flow channel in the third layer of thin film, the sixth fluid-flow channel being configured to permit fluid flow in a direction generally parallel to the third layer. The forth, fifth, and sixth fluid-flow channel are desirably configured as individual portions of a second lumen extending through the sensor.

The method may further include forming a plurality of alignment holes in penetration through the interrogation layer and disposed with sufficient precision relative to the fifth fluid-flow channel such that installation of two alignment holes in registration with respective locating pins of a cooperatingly structured interrogation device is effective to dispose the fifth fluid-flow channel at an interrogation location of the interrogation device within an accuracy of about 50 µm.

Sometimes, the manufacturing method produces a cassette structured to interface, at a first orientation, with an interrogation device to permit interrogation of a first fluid sample; and the cassette may also be structured to interface, at a second orientation, with the interrogation device to permit interrogation of a second fluid sample. In one case, the first orientation is 180 degrees rotated from the second orientation. In certain cases, the alignment holes formed in penetration through the first layer and the third layer are over-size, compared to alignment holes formed in penetration through the interrogation layer, to resist contact between material of the first layer and the third layer and the locating pins of an interrogation device.

BRIEF DESCRIPTION OF THE DRAWINGS

In the drawings, which illustrate what are currently considered to be the best modes for carrying out the invention:

FIG. 10 is an end view of the cartridge of FIG. 6;

FIG. 31 is an end view in elevation of the interrogation platform illustrated in FIG. 30;

FIG. 32 is a cross-section view taken through section 32-32 in FIG. 31 and looking in the direction of the arrows;

DETAILED DESCRIPTION OF THE ILLUSTRATED EMBODIMENTS

Figure 1:
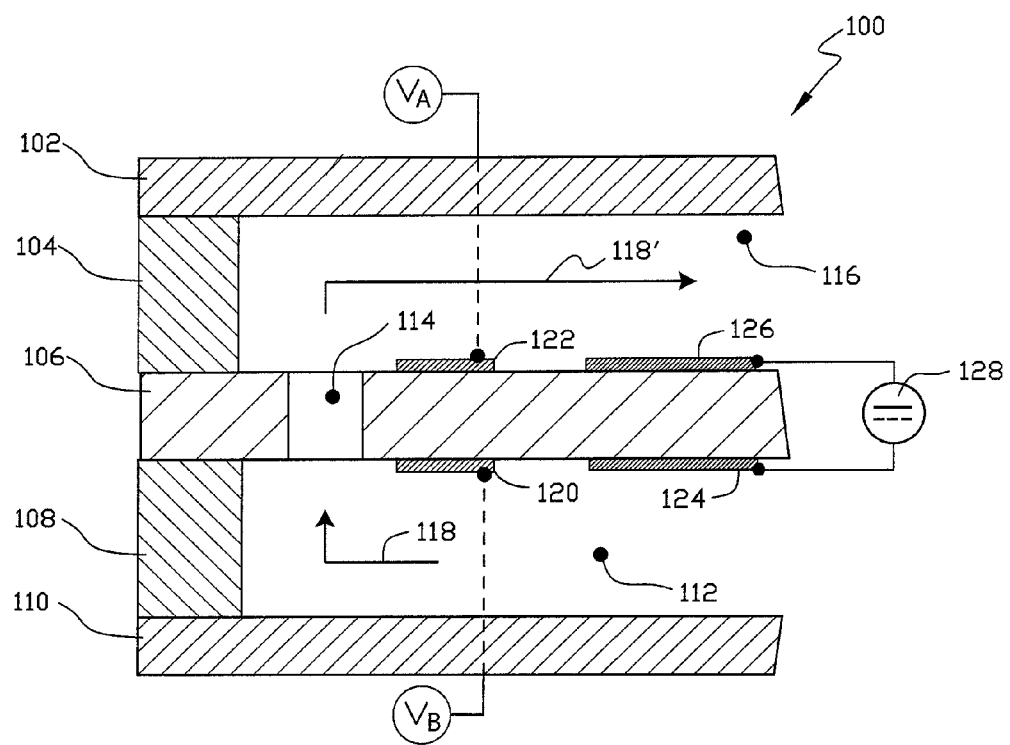
FIG. 1 is a cross-section schematic of a multi-layer sensor component structured according to certain principles of the instant invention.

Reference will now be made to the drawings in which the various elements of the illustrated embodiments will be given numerical designations and in which the invention will be discussed so as to enable one skilled in the art to make and use the invention. It is to be understood that the following description is only exemplary of the principles of the present invention, and should not be viewed as narrowing the claims which follow.

Currently preferred embodiments of the present invention provide low-cost, sometimes disposable, sometimes reusable, sensors operable to perform analyses of various sorts on particles that are carried in a fluid. Certain sensors structured according to certain principles of the instant invention may be used once, and discarded. However, it is within contemplation that such sensors may alternatively be reused a number of times.

Examples of analyses in which embodiments of the invention may be used to advantage include, without limitation, counting, characterizing, or detecting members of any cultured cells, and in particular blood cell analyses such as counting red blood cells (RBCs) and/or white blood cells (WBCs), complete blood counts (CBCs), CD4/CD8 white blood cell counting for HIV+ individuals; whole milk analysis; sperm count in semen samples; and generally those analyses involving numerical evaluation or particle size distribution for a particle-bearing fluid (including non-biological). Embodiments of the invention may be used to provide rapid and point-of-care testing, including home market blood diagnostic tests. Certain embodiments may be used as an automated laboratory research cell counter to replace manual hemacytometry. It is within contemplation to combine certain embodiments of the instant invention with additional diagnostic elements, such as fluorescence, to permit sophisticated cellular analysis and counting (such as CBC with 5-part WBC differential). It is further contemplated that embodiments of the invention may be adapted to provide a low-cost fluorescence activated cell sorter (FACS), and may be used to determine somatic cell counts in milk for the dairy industry.

For convenience in this disclosure, the invention will generally be described with reference to its use as a particle detector. Such description is not intended to limit the scope of the instant invention in any way. It is recognized that certain embodiments of the invention may be used simply to detect passage of particles, e.g. for counting. Other embodiments may be structured to determine particle characteristics, such as size, or type, thereby permitting discrimination analyses. Furthermore, for convenience, the term "fluid" may be used herein to encompass a fluid mix including a fluid base formed by one or more diluents and particles of one or more types suspended or otherwise distributed in that fluid base. Particles are assumed to have a characteristic "size", which may sometimes be referred to as a diameter, for convenience. Currently preferred embodiments of the invention are adapted to interrogate particles found in whole blood samples, and this disclosure is structured accordingly. However, such is not intended to limit, in any way, the application of the invention to other fluids including fluids with particles having larger or smaller sizes, as compared to blood cells.

In this disclosure, "single-file travel" is defined different than literally according to a dictionary definition. For purpose of this disclosure, substantially single-file travel may be defined as an arrangement of particles sufficiently spread apart and sequentially organized as to permit reasonably accurate detection of particles of interest. In general, we shoot for single particle detection at least about 80% of the time. When two particles are in the interrogation zone at the same, it is called coincidence, and there are ways to mathematically correct for it. Calibration may be performed using solutions having a known particle density (e.g. solutions of latex beads having a characteristic size similar to particle(s) of interest). Also, dilution of the particles in a fluid carrier may contribute to organizing particle travel. As a non-limiting example, it is currently preferred to use sensor devices structured to have sizes disclosed in this document for interrogation of fluid samples having a particle density of approximately between about $3 \times 10^3$ to about $3 \times 10^5$ cells/ml, where the particle size is on the order of the size of a red blood cell. The coulter principle (and biology) require a conductive fluid such as 0.9% saline. Solutions can be run that have a particle density (particles/ml) between 1000/ml to 2,000,000/ml.

FIG. 1 illustrates certain operational details of a currently preferred sensor component, generally indicated at 100, structured according to certain principles of the instant invention. As illustrated, sensor 100 includes a sandwich of five layers, which are respectively denoted by numerals 102, 104, 106, 108, and 110, from top-to-bottom. A first portion 112 of a conduit to carry fluid through the sensor component 100 is formed in layer 108. Portion 112 is disposed parallel to, and within, the layers. A second portion 114 of the fluid conduit passes through layer 106, and may be characterized as a tunnel. A third portion 116 of the fluid conduit is formed in layer 104. Fluid flow through the conduit is indicated by arrows 118 and 118'. Fluid flowing through the first and third portions flows in a direction generally parallel to the layers, whereas fluid flowing in the second portion flows generally perpendicular to the layers.

It is within contemplation that two or more of the illustrated layers may be concatenated, or combined. Rather than carving a channel out of a layer, a channel may be formed in a single layer by machining or etching a channel into a single layer, or by embossing, or folding the layer to include a space due to a local 3-dimensional formation of the substantially planar layer. For example, illustrated layers 102 and 104 may be combined in such manner. Similarly, illustrated layers 108 and 110 may be replaced by a single, concatenated, layer.

With continued reference to FIG. 1, middle layer 106 carries a plurality of electrodes arranged to dispose a plurality of electrodes in a 3-dimensional array in space. Sometimes, such electrodes are arranged to permit their electrical communication with electrical surface connectors disposed on a single side of the sandwich, as will be explained further below. As illustrated, fluid flow indicated by arrows 118 and 118' passes over a pair of electrodes 120, 122, respectively. However, in alternative embodiments within contemplation, one or the other of electrodes 120, 122 may not be present. Typically, structure associated with flow portion 114 is arranged to urge particles, which are carried in a fluid medium, into substantially single-file travel through an interrogation zone associated with one of, or both of, electrodes 120, 122. Electrodes 120, 122 may sometimes be made reference to as interrogation electrodes. In certain applications, an electrical property, such as a current, voltage, resistance, or impedance indicated at $V_A$ and $V_B$, may be measured between electrodes 120, 122, or between one of, or both of, such electrodes and a reference.

Certain sensor embodiments employ a stimulation signal based upon driving a desired current through an electrolytic fluid conductor. In such case, it can be advantageous to make certain fluid flow channel portions approximately as wide as possible, while still achieving complete wet-out of the stimulated electrodes. Such channel width is helpful because it allows for larger surface area of the stimulated electrodes, and lowers total circuit impedance and improves signal to noise ratios. Exemplary embodiments used to interrogate blood samples include channel portions that are about 0.10" wide and about 0.003" to about 0.005" high, or so, in the vicinity of the stimulated electrodes.

One design consideration concerns wettability of the electrodes. At some aspect ratio of channel height to width, the electrodes MAY not fully wet in some areas, leading to unstable electrical signals and increased noise. To a certain point, higher channels help reduce impedance and improve wettability. Desirably, especially in the case of interrogation electrodes, side-to-side wetting essentially occurs by the time the fluid front reaches the second end of the electrode along the channel axis. Of course, wetting agents may also be added to a fluid sample, to achieve additional wetting capability. The desire is to obtain fully wetted electrodes. The ratio of channel height to width is one driver. It has been determined safe to not go wider than about 0.16" in channel width for a channel layer thickness of 0.010" (channel height). Wider than that, consistency of electrode wet-out drops off.

Still with reference to FIG. 1, note that electrodes 120 and 122 are illustrated in an arrangement that promotes complete wet-out of each respective electrode independent of fluid flow through the tunnel forming flow portion 114. That is, in certain preferred embodiments, the entire length of an electrode is disposed either upstream or downstream of the tunnel forming flow portion 114. In such case, the "length" of the electrode is defined with respect to an axis of flow along a portion of the conduit in which the electrode resides. The result of such an arrangement is that the electrode is at least substantially fully wetted independent of tunnel flow, and will therefore provide a stable, repeatable, and high-fidelity signal with reduced noise. In contrast, an electrode having a tunnel passing through itself may provide an unstable signal as the wetted area changes over time. Also, one or more bubble may be trapped in a dead-end, or eddy-area disposed near the tunnel (essentially avoiding downstream fluid flow), thereby variably reducing the wetted surface area of a tunnel-penetrated electrode, and potentially introducing undesired noise in a data signal.

In general, disposing the electrodes 120 and 122 closer to the tunnel portion 114 is better (e.g., gives lower solution impedance contribution), but the system would also work with such electrodes being disposed fairly far away. Similarly, a stimulation signal (such as electrical current) could be delivered using alternatively structured electrodes, even such as a wire placed in the fluid channel at some distance from the interrogation zone. The current may be delivered from fairly far away, but the trade off is that at some distance, the electrically restrictive nature of the extended channel will begin to deteriorate the signal to noise ratios (as total cell sensing zone impedance increases).

With continued reference to FIG. 1, electrode 124 is disposed for contact with fluid in conduit flow portion 112. Electrode 126 is disposed for contact with fluid in flow portion 116. It is currently preferred for electrodes 124, 126 to also be carried on a surface of interrogation layer 106, although other configurations are also workable. Note that an interrogation layer, such as an alternative to illustrated single layer 106, may be made up from a plurality of sub-component layers. In general, electrodes 124, 126 are disposed on opposite sides of the interrogation zone, and may sometimes be made reference to as stimulated electrodes. In certain applications, a signal generator 128 is placed into electrical communication with electrodes 124 and 126 to input a known stimulus to the sensor 100. However, it is within contemplation for one or both of electrodes 124, 126 to not be present in alternative operable sensors structured according to certain principles of the instant invention. In alternative configurations, any electrode in the sensor 100 may be used as either a stimulated electrode or interrogation electrode.

Figure 2:
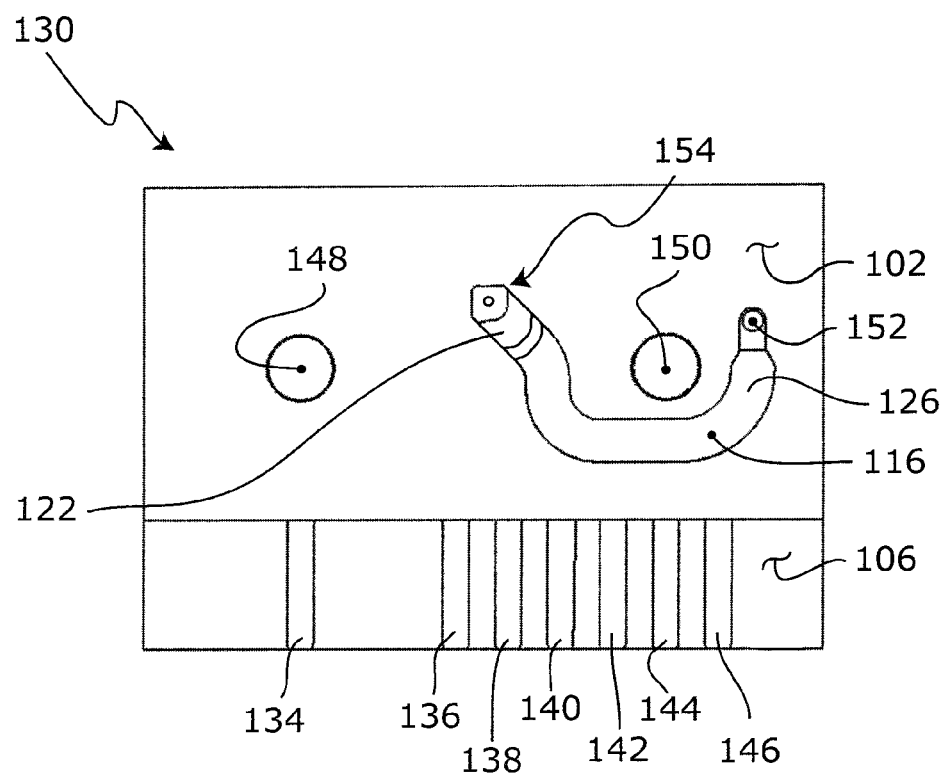
FIG. 2 is a top view of an exemplary multi-layer sensor component.

One currently preferred sensor component, generally indicated at 130, will now be described with reference to FIGS. 2-5. Sensor 130 includes five thin film layers stacked to form a thin film sandwich, similar to the embodiment depicted in FIG. 1. FIG. 2 is a top view of sensor component 130, and shows how the top cap layer 102 and top channel layer (e.g. 104, FIG. 3) form a window arranged to permit access to a portion of interrogation layer 106. In the illustrated embodiment, the exposed portion includes an edge of layer 106. The exposed surface of the edge of interrogation layer 106 carries a plurality of conductors (134 through 146, respectively) that are configured to form an electrical interface to interrogation circuitry. That is, a portion of each of conductors 134-146 is desirably exposed to form a plurality of surface connectors of an electrically communicating interface. One operable such interface may be formed in harmony with a commercially available multi-pin electrical connector, such as part No. SIB-110-02-F-S-LC, available from Samtec having a place of business located in New Albany, Ind. Other workable connector structure includes touch-down probes, and other electrically-conductive, contact-forming probes known in the art.

Also shown in FIG. 2 are alignment holes 148 and 150, respectively. Because top layer 102 is illustrated as being transparent (although such is not required for practice of the invention), electrode 126 disposed in channel portion 116 is visible. Similarly, fluid via 152 may be seen. As will be detailed further below, via 152 passes through interrogation layer 106, and permits fluid flow downwardly through the thickness of the sensor component 130. Electrode 122 is also visible, disposed in association with the interrogation zone, generally indicated at 154.

Figure 3:
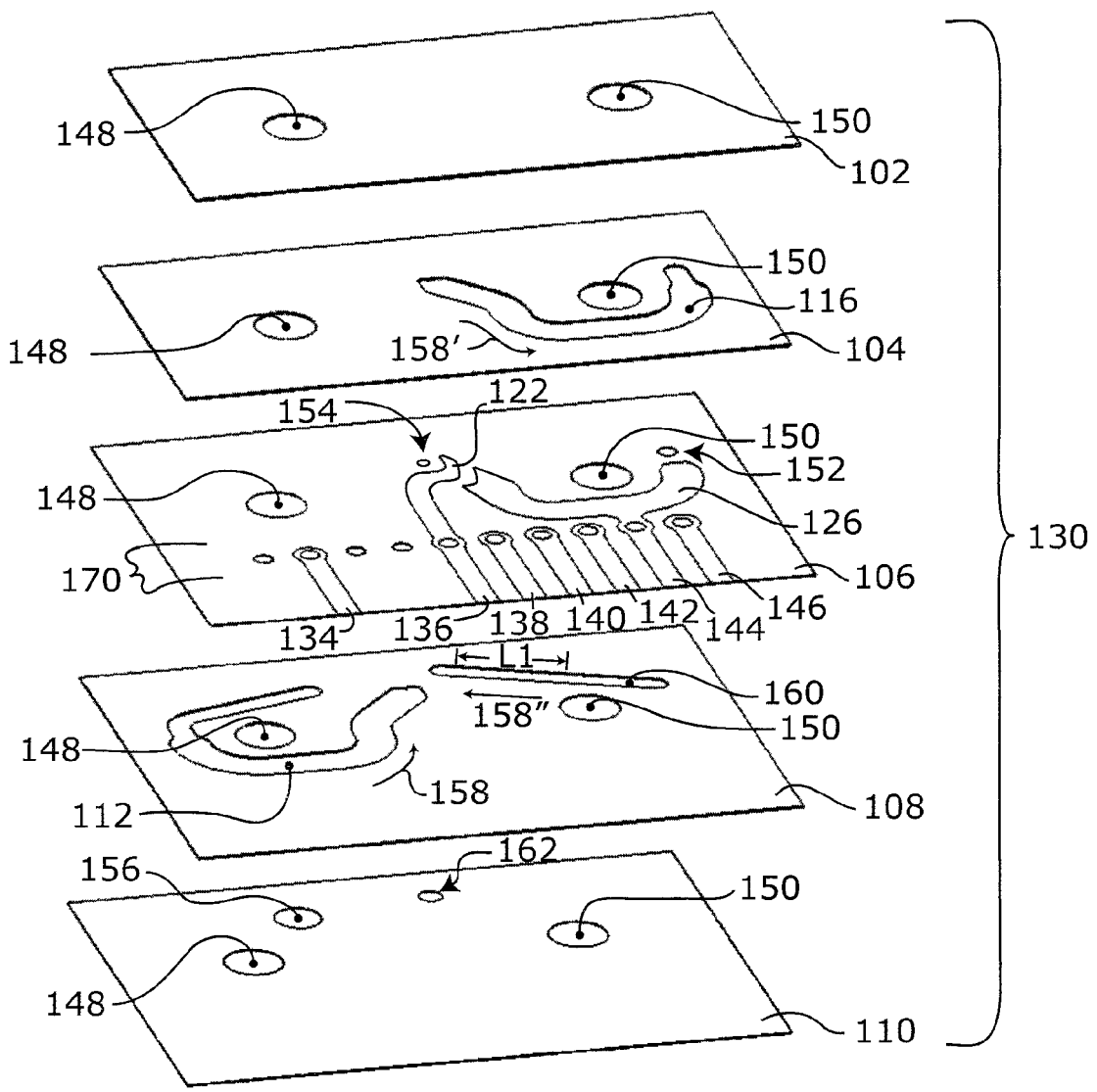
FIG. 3 is an exploded assembly view in perspective from above of the multi-layer sensor component of FIG. 2.
Figure 4:
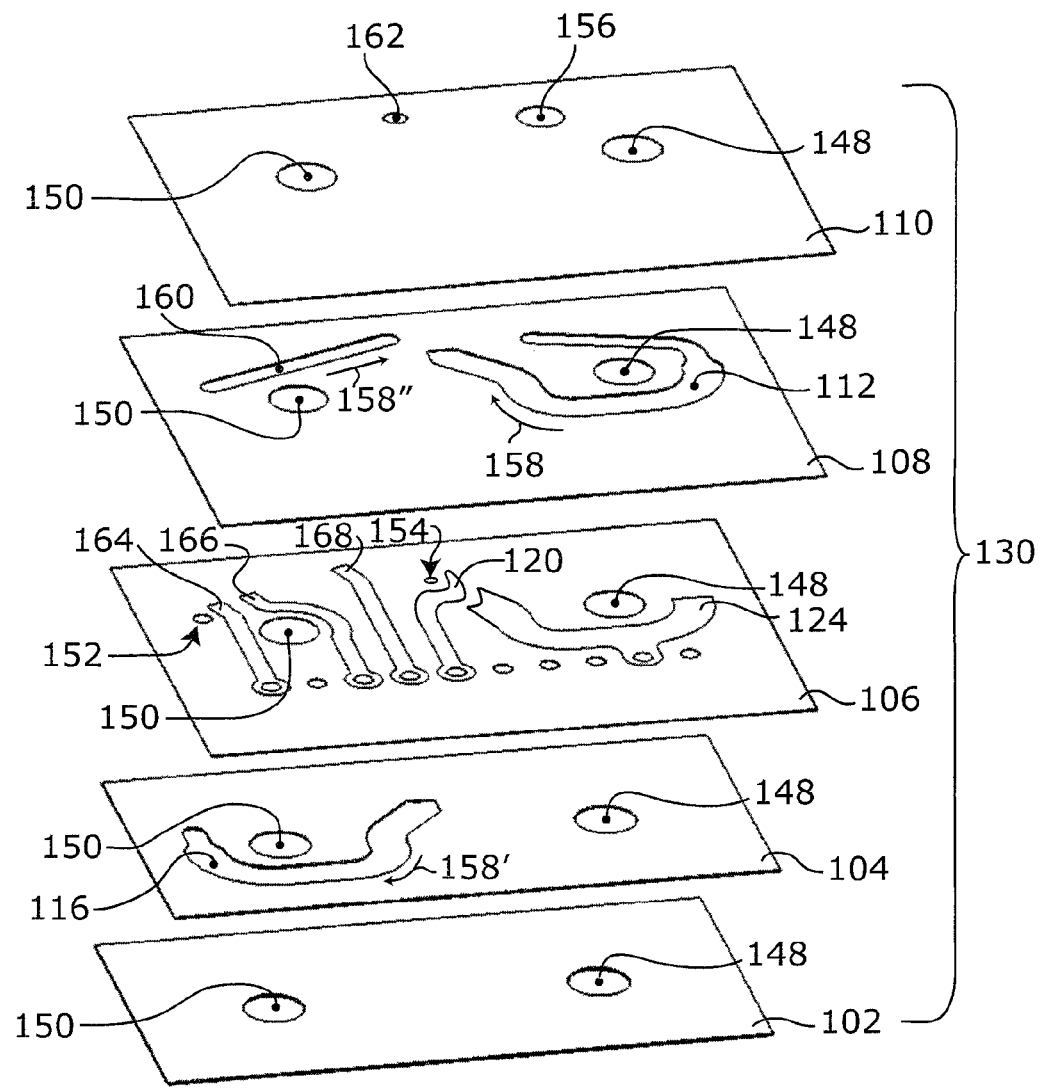
FIG. 4 is an exploded assembly view in perspective from below of the multi-layer sensor component of FIG. 2.

With particular reference now to FIGS. 3 and 4, a pair of fluid vias pass through bottom cap layer 110. Via 156 is a fluid entrance via, through which sample fluid enters the sensor component 130 for continued flow through channel portion 112, as indicated by fluid flow direction arrow 158. Channel portion 112 is disposed in layer 108 and introduces fluid into the interrogation zone 154 (or tunnel-like channel portion 114 in FIG. 1). Downstream from the interrogation zone 154, fluid flows through channel portion 116 as indicated by fluid flow direction arrow 158'. Channel portion 116 is disposed in layer 104 and communicates to via 152 passing through layer 106. Fluid via 152 communicates fluid into channel portion 160 disposed in layer 108. Fluid via 162 is a fluid exit via, through which fluid flowing through channel portion 160 may leave the sensor component 130. A direction of fluid flow in channel 160 is indicated by arrow 158".

Figure 5:
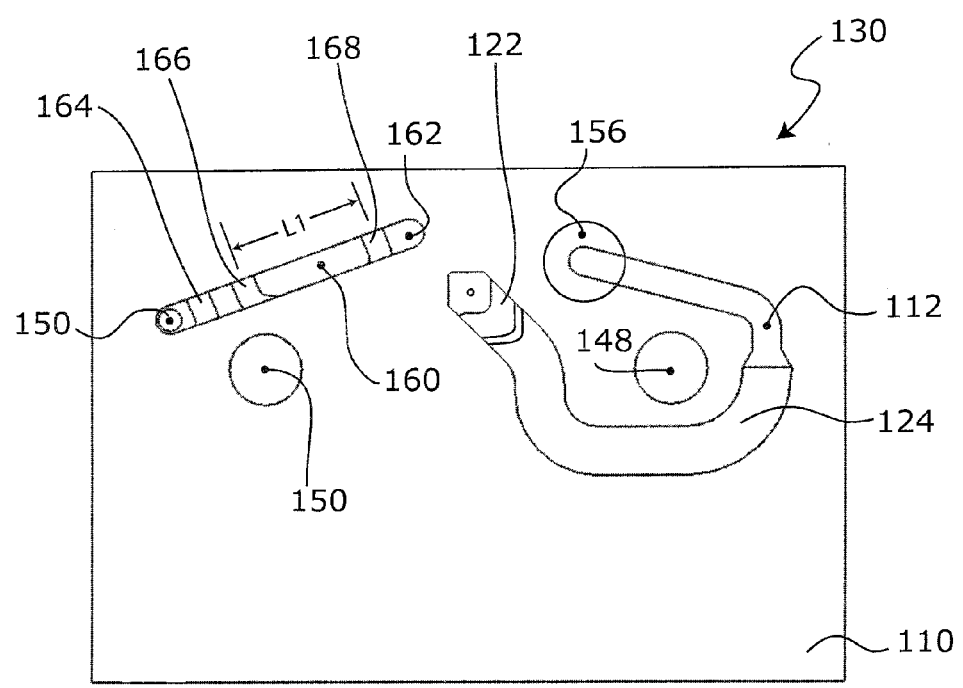
FIG. 5 is a bottom view of the multi-layer sensor component of FIG. 2.

As best seen with reference to FIGS. 4 and 5, certain embodiments of a sensor component 130 may include one or more additional and optional electrodes. Layers 102 and 104 are illustrated as being transparent, although such is not required for practice of the invention. As illustrated, electrodes 164, 166, and 168 are disposed on layer 106 and are arranged for contact with fluid carried in channel portion 160. Electrode 164 is in electrical communication with conductor 146; electrode 166 is in electrical communication with conductor 142; and electrode 168 is in electrical communication with conductor 140. Such optional electrodes may be used, for examples, to verify the presence of sample fluid at one or more known locations in sensor 130, to estimate the rate of fluid flow through the sensor, and/or as start or stop triggers for an activity such as data acquisition.

It should be noted that certain electrodes carried by sensor 130 (e.g. 120, 124, 164-168), are in electrical communication with their respective conductor that is disposed on an opposite side of layer 106 by way of a conductive path disposed through a respective electrical via 170 (see FIG. 3). Such conductive path is conveniently formed during a laminating or metallizing step during manufacture of the sensor component. In any case, it should be appreciated that a complex pattern of electrodes can be disposed to interrogate fluid in 3-dimensional space, even in the illustrated case where the electrodes are carried by a single metallized layer.

The conductive elements forming conductors (e.g. 134-146) and/or electrodes (e.g. 120-126) must simply conduct electricity, and can include one or more metal, such as Copper, Silver, Platinum, Iridium, Chromium, and Gold, or alloys, or multiple layers of metals or alloys. The vias 170 permit conduction of electricity from top to bottom through spacer layer 106, and enable surface conductors to be disposed on only one side of the spacer layer, for convenient interface with a commercially available electrode interface (i.e. connector). Of course, it is realized that certain interface probe-electrodes of an interrogation platform may be structured to avoid vias on the sensor, e.g. that surface electrodes can be provided on both sides of the spacer layer, in alternative sensor constructions.

An electrical property at an electrode may be monitored to determine arrival of fluid at that electrode. For example, the impedance measured at an electrode undergoes a significant change in value as the wave-front, or the leading edge, an electrolyte fluid passes over the electrode. In one currently preferred use of the sensor component 130 (see FIG. 4), a stimulus electric signal (such as a 1 kHz square wave) is applied to electrode 164. A sudden change in the impedance values measured at electrodes 166 and 168 indicates the successive arrivals of the wave-front of the sample fluid at each respective electrode. In the illustrated embodiment 130, first verification of fluid at electrode 166 ensures that sample fluid is in place for interrogation, and a test run can begin. Feedback from electrode 166 may therefore serve as a first trigger to begin interrogation of the fluid sample.

A change in impedance at electrode 168 indicates the wave-front has reached that electrode as well. A time differential between the impedance changes at electrodes 166 and 168 can be used, in harmony with a known volume therebetween, to estimate a fluid flow rate through the sensor component 130. The volume between electrodes 166 and 168 may be calculated by integrating the function of the cross-section area of channel portion 160 along the length L1 of such channel portion disposed between those electrodes. It is currently preferred to simplify such calculation by holding the cross-section of channel portion 160 constant between electrodes.

Electrodes, such as 166 and 168, may be disposed as first and second triggers operable to indicate respective start and stop signals based upon detection of a fluid boundary. The first and second triggers can be located to have locations of effective operation that are disposed spaced apart by a lumen defining a known volume. Such triggers may be used, for non-limiting example, to start and stop data acquisition for a sample having a known volume. It is preferred for cooperating trigger electrodes to have substantially the same conformation (e.g. wetted area and axial length), to promote consistent electrical response of each subsequent downstream trigger. Sometimes, the channel may be narrowed in the vicinity of an electrode to reduce possible variations in the shape of the fluid front as it makes contact with the electrode.

A sensor 130 may be formed from a plurality of stacked and bonded layers of thin film, such as a polymer film. In an exemplary sensor component 130 used in connection with interrogation of blood cells, it is currently preferred to form top and bottom layers 102 and 110 from Polyamide or Mylar film. A workable range in thickness for Polyamide layers is believed to be about 0.1 micron to about 500 microns. A currently preferred Polyamide layer 102, 110 is about 52 microns in thickness. It is further within contemplation that a pair of top and/or bottom layers can be formed from a single layer including fluid channel structure formed e.g. by etching, molding, or hot embossing.

It is currently preferred to make the spacer layer 106 from Polyamide also. However, alternative materials, such as Polyester film or Kapton, which is less expensive, are also workable. A film thickness of about 52 microns for spacer layer 106 has been found to be workable in a sensor used to interrogate blood cells. Desirably, the thickness of the spacer layer is approximately on the order of the particle size of the dominant particle to be interrogated. A workable range is currently believed to be within about 1 particle size, to about 15 times particle size, or so.

Vias 170 are typically formed in the layer 106 prior to dual-sided deposition of the conductive elements onto such layer, although alternative manufacturing techniques are workable. Alignment apertures 148, 150 and via 152 may be formed at the same time as vias 170, or subsequent to the metallizing step. Such void elements, and channel portions, may be formed by cutting through the respective layer with a laser, water jet, die stamping, drilling, or by some other machining technique. Deposition of conductive film elements to layer 106 may be effected using well-known metal-deposition techniques, including lamination. Metal sheets may be laminated to a polymer layer using thin adhesive. Double clad sheets formed in such manner are commercially available, and can be patterned as desired to form electrodes. It is believed that workable sensors can be made having test electrodes that are 0.5 microns in thickness, or perhaps even less. Electrodes for use in currently preferred blood cell sensors may be up to about 36 microns in thickness. Sometimes, a pair of metals, such as Cu or Cr and Au may be deposited in the current process. The Cu or Cr layer may be thin, typically goes on first, and acts as a bonding layer between the polymer film and the Au. It is currently preferred to configure the electrodes and conductive elements by wet etching subsequent to deposition of the electrically conductive material.

Impedance at the electrode/electrolyte interface is proportional to wetted electrode surface. Electrodes may be configured having a desired useful size of surface area disposed for contact with fluid in a channel. It is currently preferred to apply a stimulation signal to stimulated electrodes to cause at least about 0.1 mA RMS current flow through the interrogation zone. The currently preferred signal is at 100 kHz, although signals at lower frequency or higher frequencies, such as 200 k Hz, or more, are operable. The surface area of the stimulated electrodes are sized to accommodate a desired current flow and signal frequency. It is currently believed that electrodes should be sized to have a current density of less than about 5 mA/cm$^2$.

In one embodiment of sensor 130 adapted to impart a constant 1 mA RMS current stimulation at about 100 kHz, interrogation electrodes 120, 122 have a wetted surface area of about 0.036 cm$^2$, and stimulated electrodes 124, 126 have a wetted surface area of about 0.45 cm$^2$. In such case, it is thought that the stimulated electrodes 124, 126 could be reduced in size to about 1/5 cm$^2$, or less, without suffering a lack of performance due to degradation of the electrode during such stimulation.

The channel portion 114 is typically laser drilled through layer 106 (and any electrodes carried thereon that are also disposed in the fluid path). A diameter of 35 microns for channel 114 is currently preferred in certain preferred embodiments to urge blood cells toward single-file travel through the interrogation zone 154. Other cross-section shapes, other than circular, can also be formed during construction of channel 114. Naturally, the characteristic size of the orifice formed by drilling channel 114 will be dependent upon the characteristic size of the particles to be characterized or interrogated. Counter-boring can be performed on thicker layers to reduce the "effective thickness" of the sensing zone.

Alignment holes 148, 150 passing through each layer may be used to align the various layers using guide pins during assembly of the plurality of layers. A double-sided adhesive polymer film is currently preferred as a material of composition for combination bonding-channel layers 104 and 108. Layers 104 and 108 in a currently preferred sensor 130 are made from double-sided Polyamide (PET) tape having a thickness of about 0.0032 inches. Alternatively, a plain film layer may be laminated to an adjacent plain layer using heat and pressure, or adhesively bonded using an interposed adhesive, such as acrylic or silicone adhesive.

Figure 6:
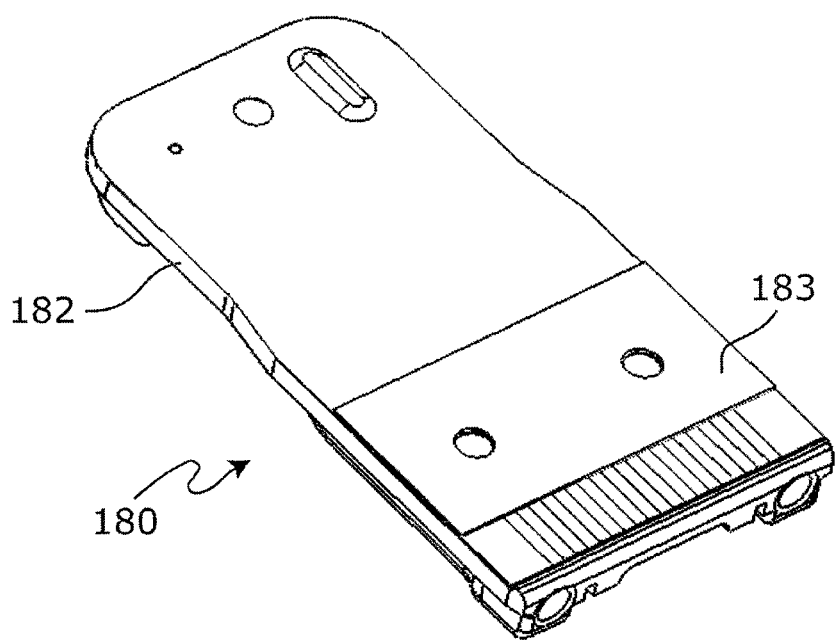
FIG. 6 is a view in perspective from above of a sensor component carried by a cartridge.

A currently preferred sensor structured according to certain principles of the instant invention is generally indicated at 180 in FIG. 6, and may sometimes be characterized as a cartridge. Cartridge 180 includes a base 182 on which to hold a sensor component, such as some sort of thin film sensor 183. A workable base may be formed by injection molding a plastic, or plastic-like, material. It is preferred to configure base 182 having a small size to reduce a required volume of constituent material, but still form a sensor 180 that is sufficiently large to facilitate its handling and manipulation under control of a human hand.

Figure 7:
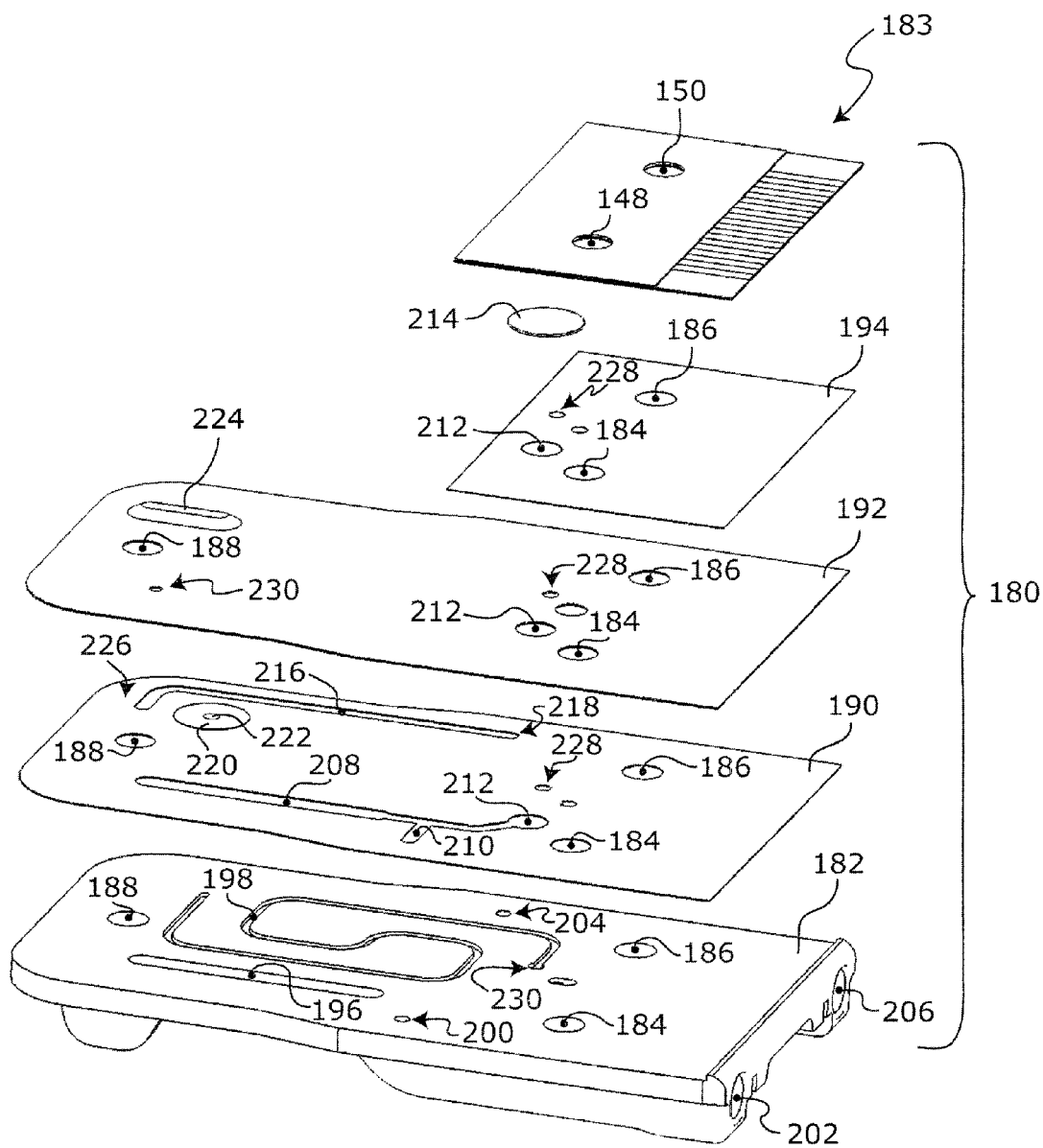
FIG. 7 is an exploded assembly view in perspective from above of the cartridge of FIG. 6.
Figure 8:
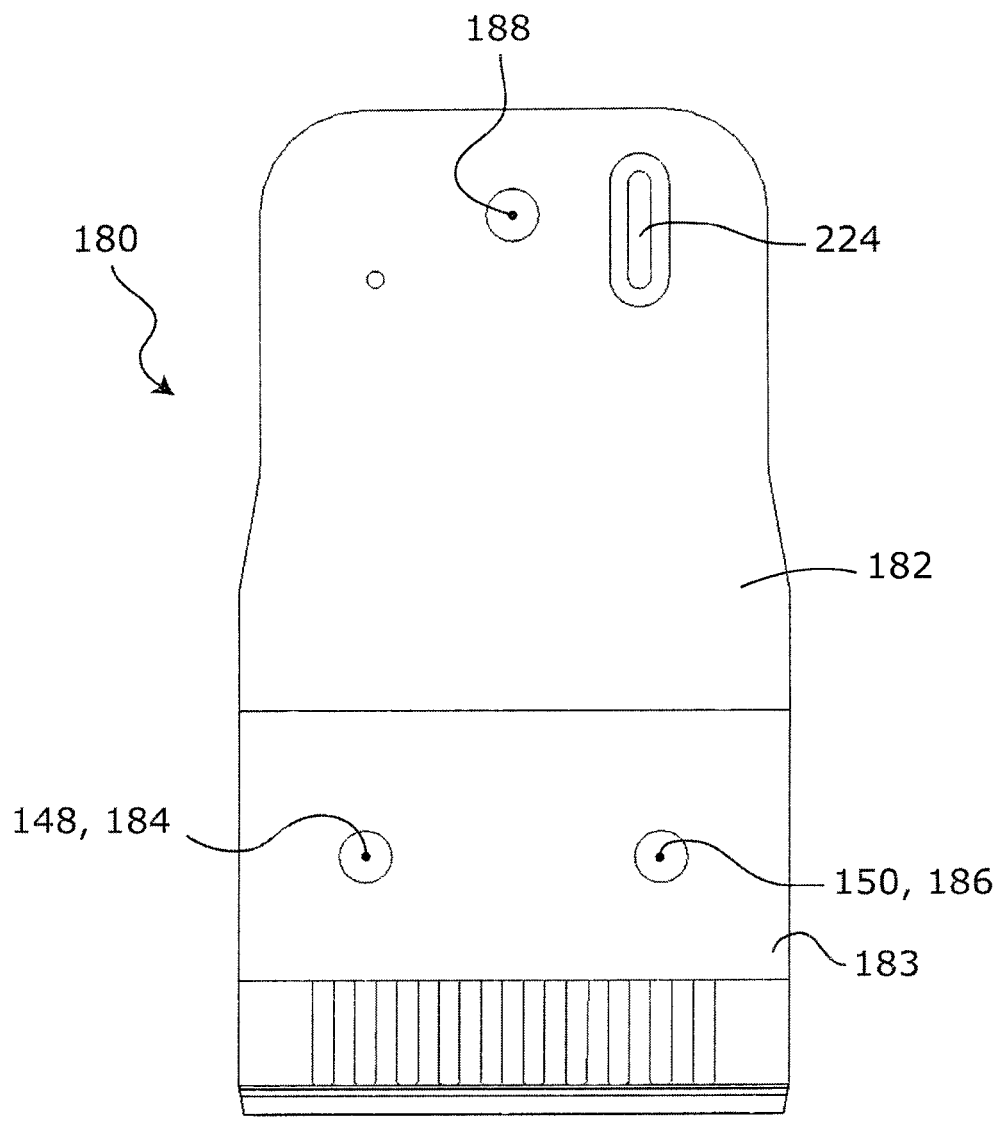
FIG. 8 is a top view of the cartridge of FIG. 6.
Figure 9:
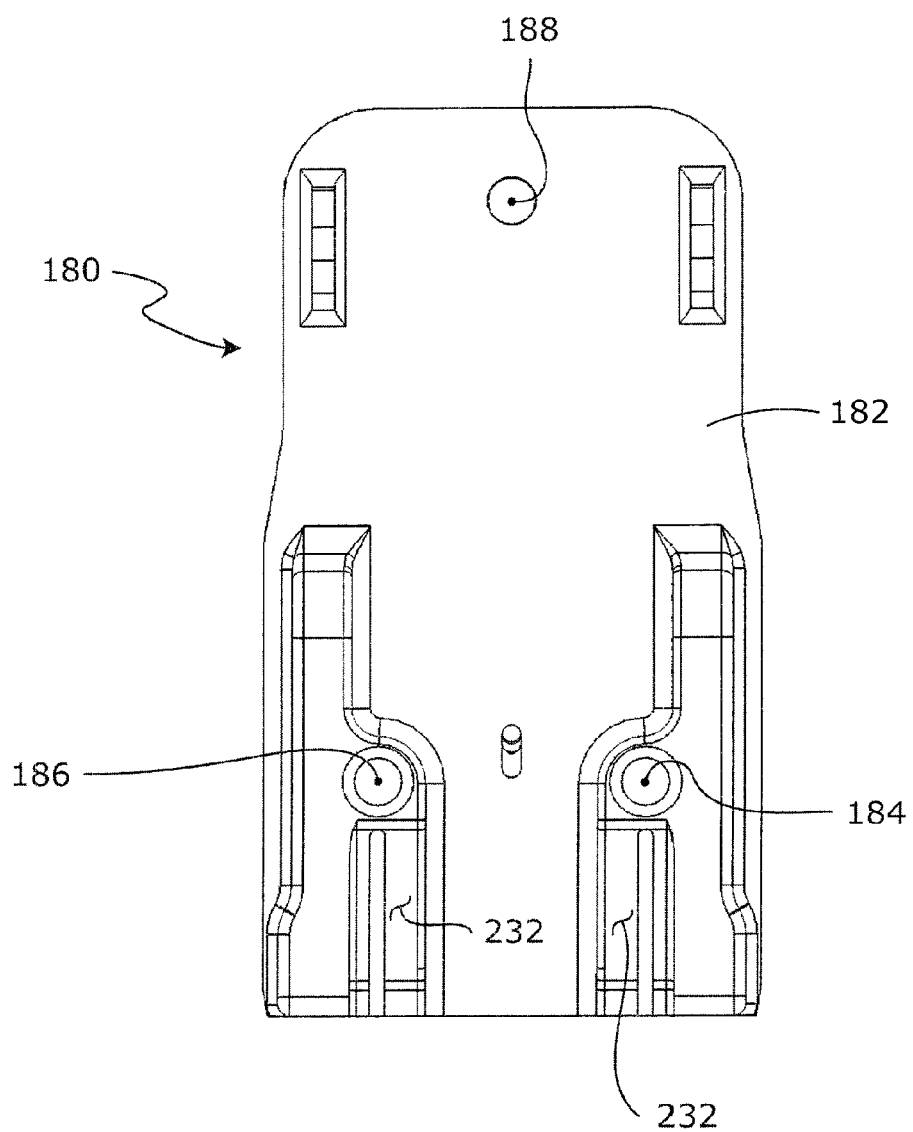
FIG. 9 is a bottom view of the cartridge of FIG. 6.
Figure 11:
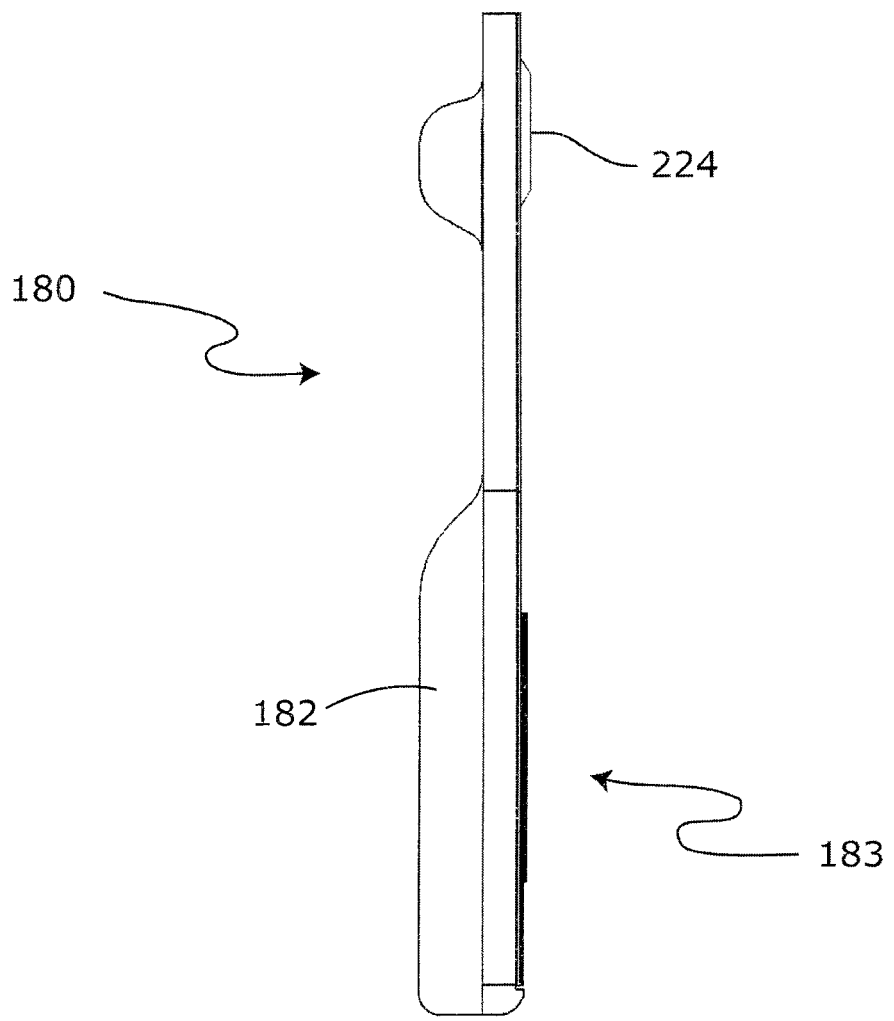
FIG. 11 is a side view of the cartridge of FIG. 6.

With reference now to FIG. 7, base element 182 includes alignment holes 184, 186, and 188, which also extend to pass through channel layer 190, cap layer 192, and adhesive layer 194. Holes 184 and 186 are configured and arranged to cooperate with alignment holes 148 and 150, respectively, to permit component alignment using pin elements of a common fixture during assembly of the sensor 180. Base element 182 also holds sample receiving chamber 196, and processed fluid chamber 198. Vent aperture 200 is in fluid communication through base 182 with vent connection access port 202. Similarly, vacuum aperture 204 is in fluid communication through base 182 with vacuum connector access port 206.

Channel layer 190 may be formed from a thin film of polymer film, similar to layers 104, 108 of the sensor 130. Preferably, layer 190 is made from a two-sided adhesive tape, such as Polyamide tape. Layer 190 includes cut-out area shaped to form additional void elements, including channel 208, a portion of which augments a volume provided by chamber 196 in which to receive a fluid sample. Transverse portion 210 of channel 208 communicates to vent aperture 200, effective to permit escape of air from chamber 196 during infusion of a sample for interrogation.

Continuing to refer to FIG. 7, aperture 212 extends as a fluid-flow channel or via through layers 190, 192 and 194 effective to introduce fluid received from chamber 196 into sensor component 183. An optionally enlarged portion of channel 212 permits fluid to spread out over a sufficiently large filter area prior to passing through optional filter element 214 and entering sensor element 183. It typically is desirable to include a filter element 214 to resist entrance into the interior of sensor component 183 of clots or debris that might plug channel portion 114. A preferred filter element 214 resists passage of particles larger than those approaching the characteristic size of the interrogation zone 154. A workable filter 214 includes a Nylon Net Filter NY30 available from Millipore Cat: NY3004700, which has filtering pores that are about 30 microns in size. Desirably, the filter essentially consists of openings having a characteristic size that is smaller than a characteristic size of a minimum cross-section of the interrogation zone.

Still with reference to FIG. 7, layer 190 also includes vacuum channel 216, which communicates at end 218 with vacuum aperture 204. As will be discussed in more detail below, fluid may be transported through certain conduits of sensor 180 using a vacuum source that may be connected to port 206.

In certain preferred embodiments, a barrier element 220 is disposed in association with aperture 222 passing through layer 190. A workable barrier element 220 permits escape of air from chamber 198, but resists escape of fluid from such chamber. A preferred barrier 220 includes a PTFE gasket, such as a 0.2 micron pore size Fluoropore, FGLP, which can be purchased from Millipore Cat. No. FGLP01300. Gasket 220 is illustrated in FIG. 7 as being installed in a preferred blocking position on the bottom of layer 190, but may be disposed in a blocking position on either side of layer 190. Barrier 220 is an exemplary embodiment of flow termination structure disposed downstream from the interrogation zone and arranged to resist flow of fluid beyond a boundary associated with the microfluidic sensor. Other operable flow termination structure includes porous materials that turn to gels when wet; hydrophobic porous membranes or plugs; and very small laser drilled holes in films (e.g. <10 microns).

Continuing to refer to FIG. 7, an exemplary layer 192 may be made from polymer film, and functions as a cap layer, similar to layer 110 of sensor component 183. An embossed portion 224 is formed in layer 192 to create a simple channel structure through which air can communicate between end 226 of vacuum channel 216 and aperture 222. The vacuum-side fluid conduit communicating between port 206 and a sensor exit (such as exit via 162 of sensor 130), is completed by way of aperture 228, which forms a fluid conduit or via extending from end 230 of chamber 198, through layers 190, 192, and 194, for communication with a fluid exit via of an installed thin film sensor component 183.

In use of the device, a micro-pipette tip may be inserted for fluid-tight reception into sample-receiving aperture or port 230. A raw fluid sample can then be infused from the micro-pipette into chamber 196, while air is permitted to escape through channel 210 and vent port 202. The size for a raw fluid sample for characterization of blood cells in one representative device is 50 µl, although the sensor conduits and chambers may be sized to accommodate samples having an alternative desired size. Vent port 202 is then occluded, either manually or using an automated structure. A vacuum source is then applied to port 206 to promote fluid flow from holding chamber 196, through channel 208, aperture 212, optional filter 214, and into a fluid entrance of the sensor component.

After flowing through the sensor component, fluid is drawn through aperture 228 and into holding chamber 198. Once chamber 198 is filled, fluid is barred from further flow by barrier element 220, which is one example of operable flow termination structure that resists additional flow. The volume of fluid encompassed by chamber 198 can help to determine a known volume for processed fluid. In the representative device, the processed fluid volume, defined by chamber 198 in combination with a small upstream volume contained in conduit structure stretching to a fluid-front presence verification structure, such as electrode 166 (see FIG. 4), is 25 µl.

Additional details of construction of an exemplary cartridge 180 are illustrated in FIGS. 8-11. Notably, ramp structure 232, best seen in FIGS. 9 and 10, can be helpful to assist in coupling the cartridge with certain interrogation platforms. Other structure associated with the base 182, such as alignment holes 186 and 188, may also be employed to assist in coupling a cartridge with an interrogation platform.

An interrogation platform desirably provides three functions; 1) apparatus configured in harmony with the sensor (or cartridge, cassette, etc.) effective to detect particles of interest, 2) fluid-flow control, and 3) alignment. A workable, and currently preferred interrogation platform is indicated generally at 240 in FIGS. 12-15.

Figure 13:
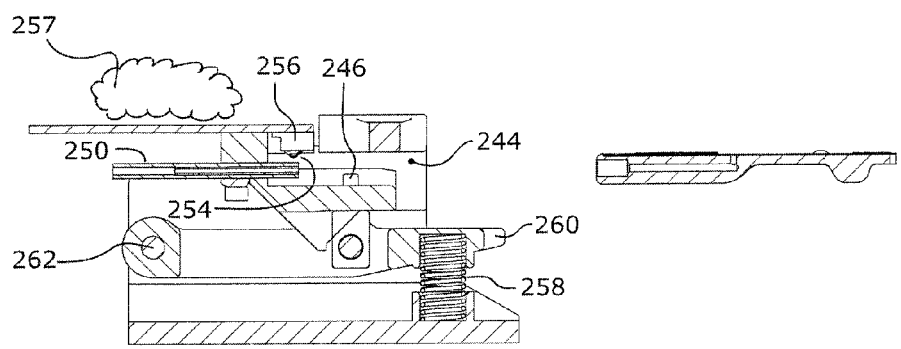
FIG. 13 is a cross-section view, taken through section 13-13 in FIG. 12, and looking in the direction of the arrows.

A cartridge 242 is illustrated in position for its insertion in registration with socket 244 (see FIG. 13). As the cartridge is inserted into the socket 244, ramps 232 on the bottom side of the cartridge body press the two alignment pins 246 down. The cartridge 242 then comes into contact with the vent and vacuum connectors, 248 and 250, respectively.

In the illustrated platform 240, the vent connector 248 and vacuum connector 250 are made from silicone rubber tubing. The rubber tubes mate with respective connection ports (e.g. 202 and 206, see FIG. 10) to form an airtight seal. The silicone rubber tubing is supported on the inside by a smaller, more ridge piece of tubing. The rigid, internal tubing imparts the required mechanical stability while the soft, flexible rubber tubing conforms to make an airtight seal. This airtight seal is actually made because the rubber tube extends sufficiently to contact the bottom of the cartridge mating hole before the cartridge is fully seated. When the cartridge is inserted slightly further into the interrogation platform, the rubber tube is forced to expand radially outward, thereby making an airtight seal against its receiving socket (e.g. 202 or 206).

Figure 12:
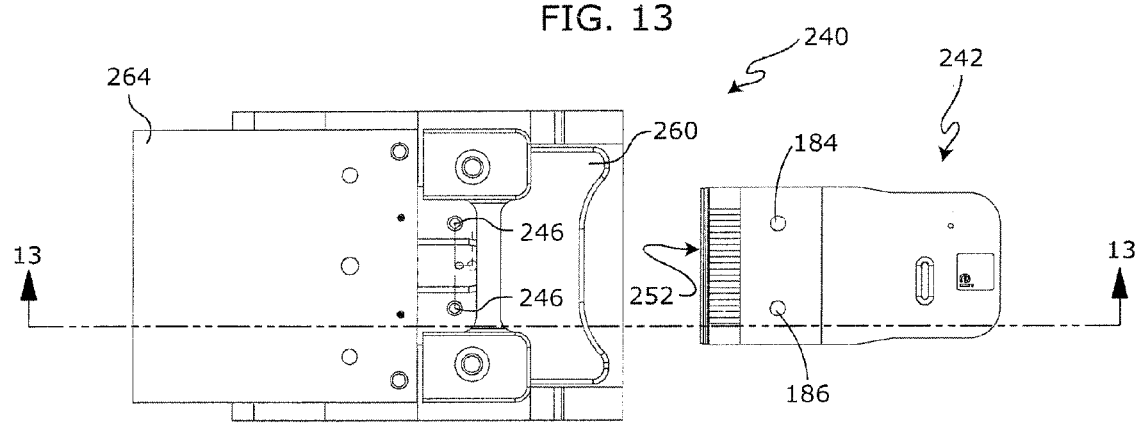
FIG. 12 is a top view of a cartridge in position for its installation into an interrogation platform.
Figure 14:
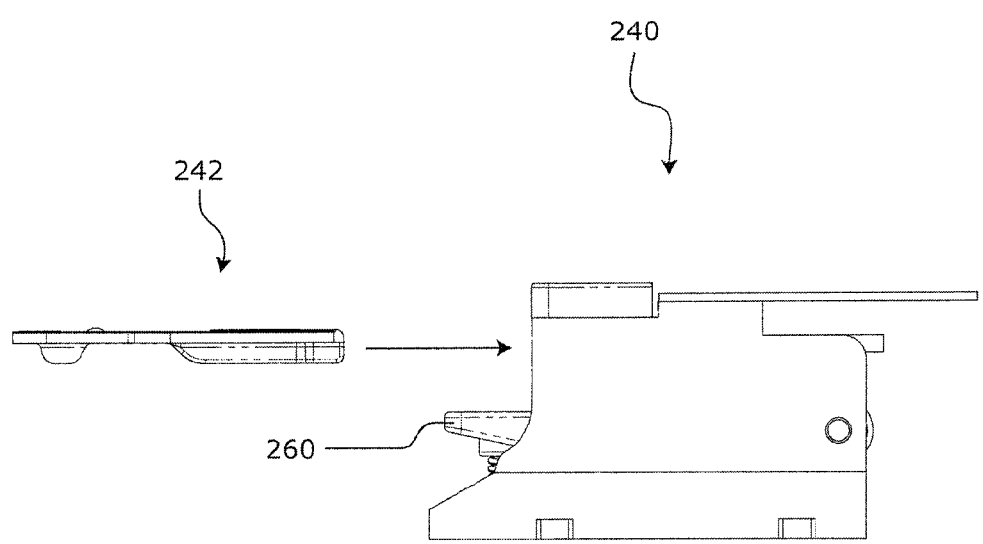
FIG. 14 is a side view of the assembly of FIG. 12.
Figure 15:
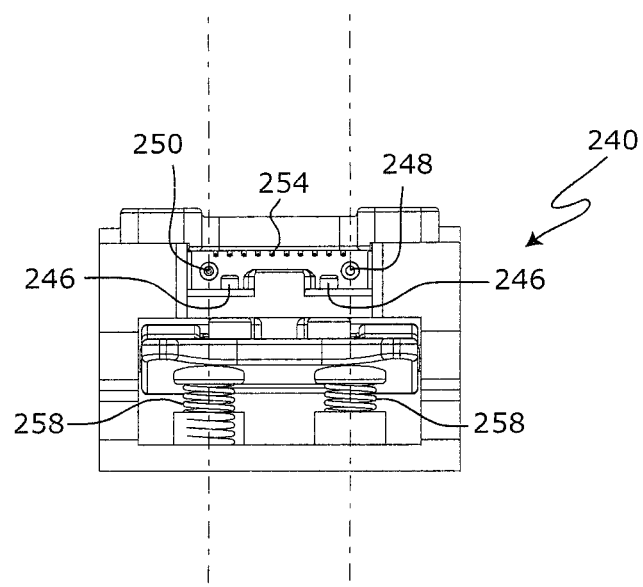
FIG. 15 is a cartridge-loading end view of the interrogation platform of FIG. 12.

When seated in socket 244, the electrical contact pads (on the top of the cartridge and generally indicated at 252 in FIG. 12) contact biased pins 254 of the electrical connector 256. The electrical connector 256 places the sensor 242 in electrical communication with test circuitry 257 that is typically carried by an interrogation platform and is adapted to interrogate particles passing through the sensor.

When the cartridge 242 is fully inserted, the alignment pins 246 seat inside the alignment holes 184, 186 in the bottom of the cartridge via force imparted by springs 258. The cartridge is now fully engaged, aligned, and ready for testing. To remove a cartridge, the release latch 260 is pressed downward, thereby retracting the alignment pins 246 from the cartridge body as the latch rotates about pivot axle 262. The cartridge can then be easily pulled out of the interrogation platform.

The interrogation platform may include circuitry that may be carried on printed circuit board 264, or otherwise arranged to communicate with the sensor. A plurality of different test circuits may be provided by simply exchanging the circuit board 264 to one having the desired configuration. Such circuitry may include structure arranged to apply a first time-varying stimulus signal to stimulated electrodes. A currently preferred first stimulus signal is a constant current source, although a constant voltage source is also workable. A preferred first stimulus signal is about 100 kHZ 1 mA rms. A second stimulus signal may be provided and coupled to electrodes adapted to detect presence of a fluid wave-front. A preferred second signal is a 1 k Hz square wave input to a first electrode and permitting measurement of an electric property by using at least one other electrode. Impedance or voltage may be evaluated at or between measurement electrodes. Sometimes, a differential may be measured between electrodes. Other times, ground may be enforced at one electrode, and an electrical property measured at the other electrode. It is within contemplation for one electrode to be eliminated entirely, and use a ground reference.

Figure 16:
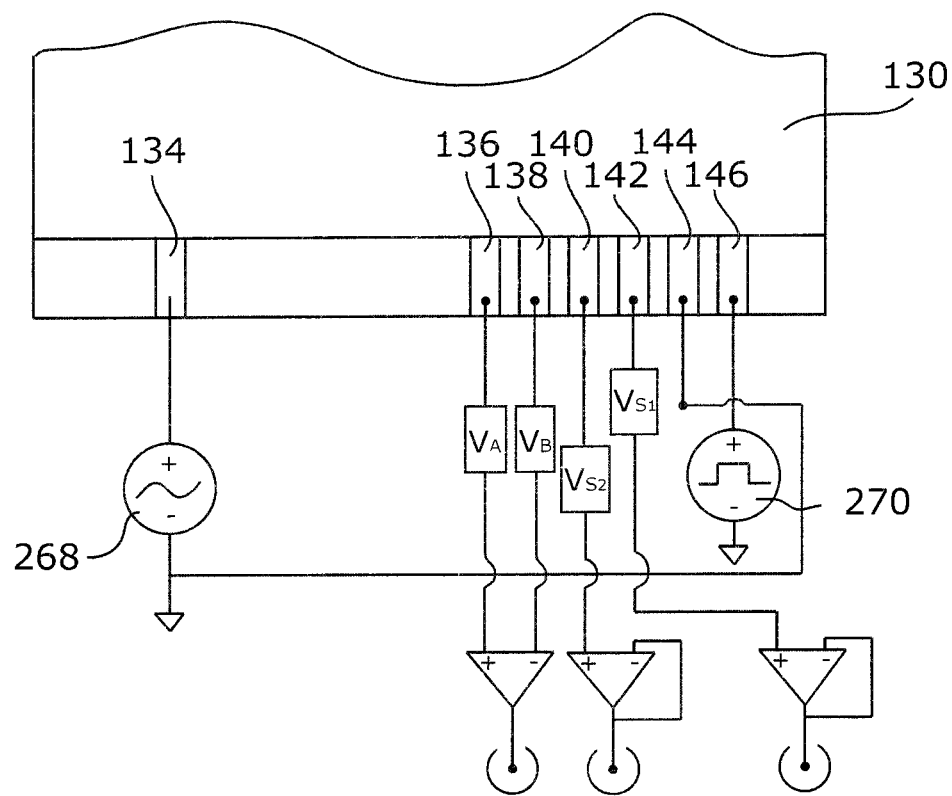
FIG. 16 is a schematic of a workable interrogation circuit for use with a sensor such as illustrated in FIG. 6.
Figure 17:
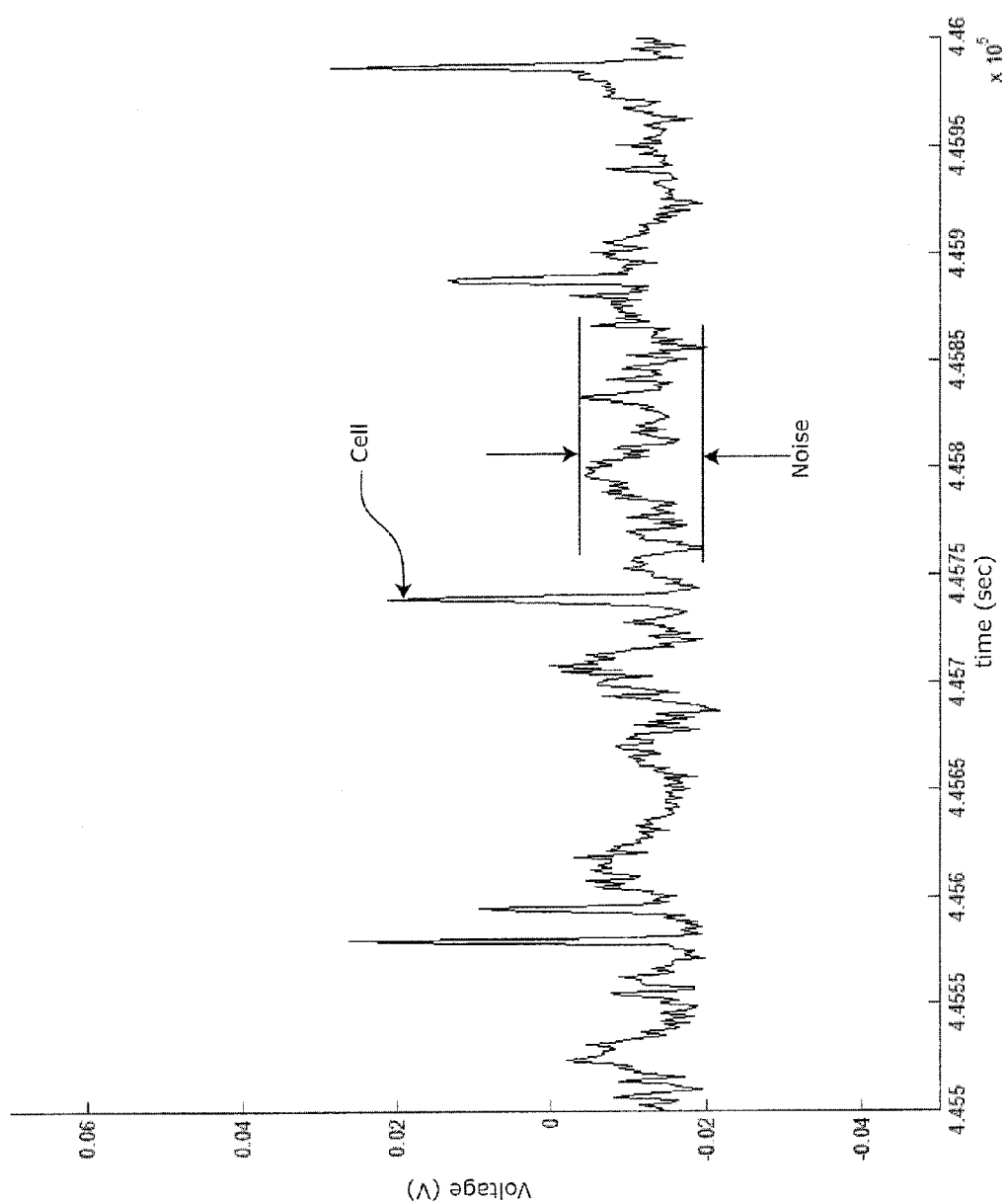
FIG. 17 is an X-Y plot representative of certain electrically-based interrogation data obtainable using certain preferred sensor embodiments.
Figure 18:
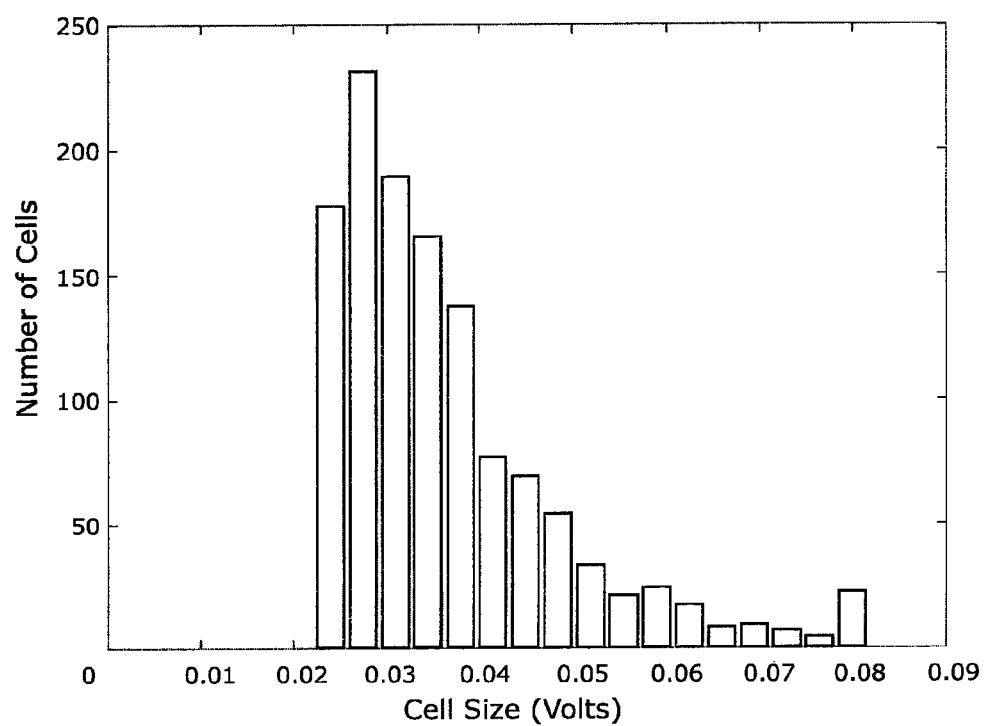
FIG. 18 is a bar chart depicting data related to particle size distribution that may be obtained using certain preferred sensor embodiments.

FIG. 16 illustrates one workable interrogation circuitry adapted to interrogate a sensor 130. In the cell interrogation loop, a signal generator 268 is applied between conductors 134 and 144. It has been determined that electrical ground may be enforced at one of such conductors. In current sensors adapted to interrogate blood cells, it is preferred to apply a constant RMS current signal of about 1 mA at about 100 kHz. Values for voltages $V_A$ and $V_B$ are measured at conductors 136 and 138, respectively for calculation of a differential voltage across the cell interrogation zone. It has been determined that an electrical ground may be enforced at one such conductor, and the voltage directly measured at the other conductor may be used in place of a true differential voltage. It is also possible to allow one electrode to "float" (i.e. not be connected to anything) and measure the voltage compared to a different electrode. In the fluid detection loop, a signal generator 270 can be applied between conductor 146 and each of conductors 140 and 142. The impedance or voltage signal $V_{S1}$ and $V_{S2}$ can then be measured to determine the presence of the fluid wave-front. A sudden drop in the measured impedance indicates presence of the wave-front of electrolytic fluid. A workable signal includes a square-wave at about 1 kHz at about 3 volts. FIGS. 17 and 18 present electrically-based interrogation data that may be collected using certain preferred sensors.

In a method of using one embodiment of a device to count cells in a blood sample, 50 micro-liters of fluid are added to the sensor via a pipette-tip hole which is sized to form an air tight fit with the pipette tip. As the sample enters the sample storage channel, air displaced by the fluid exits the cartridge through a vent port that connects to the interrogation platform. The sample can be added to the cartridge before or after it has been connected to the interrogation platform. Once the sample is in the cartridge, and the cartridge is installed in an interrogation platform, the user starts the test by activating one or more "start" control of the system. The "start" causes a valve connected to the vent port to close, thereby not allowing the sample to flow into the vent port. The "start" also opens the vacuum valve to start pulling the fluid sample into the sensor. Because the vent is sealed, fluid is drawn from the sample storage chamber and though the thin film sensor component. A "start" may also initiate a stimulus (e.g. 1 kHz) to the sample detection electrodes embedded in the thin film sensor component. Once the fluid is through the sensing orifice and has wet the stimulus and measurement electrodes, it flows over a pair of sample detection electrodes. As the fluid wave-front reaches the detection position at the second electrode, a large drop in electric impedance is detected and the constant current source is activated (e.g. 100 kHz @ 1 mA). A differential voltage is measured across the interrogation zone (4 electrode configuration, currently preferred) and used to determine cell size (and/or count) subsequent to the time of wave-front detection. Fluid continues to flow until it reaches the end of the "dead-end" channel and no more cells are detected. The volume that is processed in a test run is determined by the volume accommodated downstream of the wave-front detection location, and is 25 micro-liters in a preferred single-use device. The method may also include monitoring one or more additional sample detection electrode placed further down the channel, i.e. to determine the approximate flow rate during, or prior to starting, the cell counting.

Figure 19:
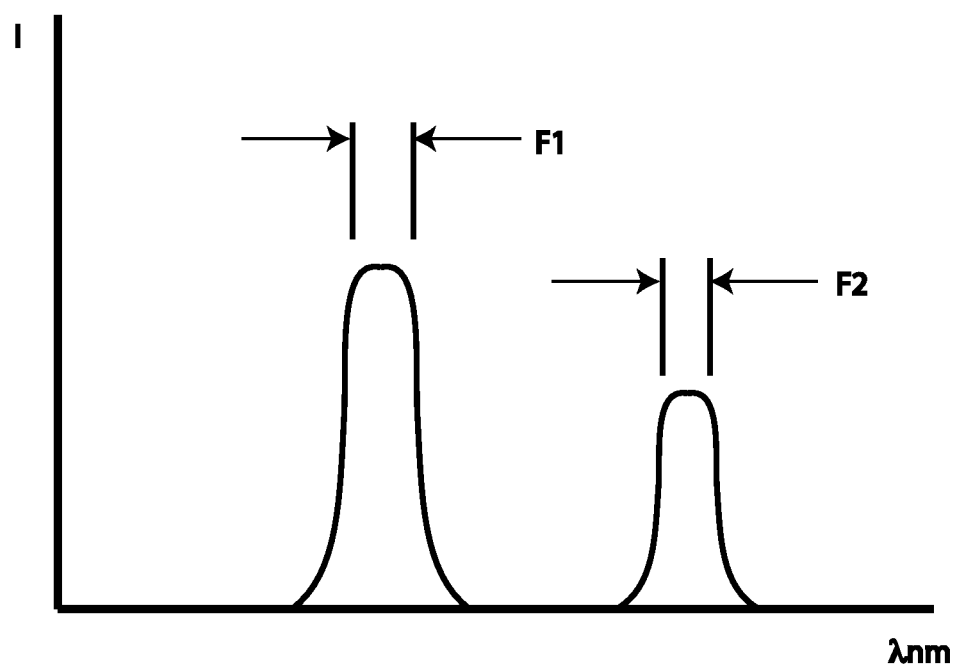
FIG. 19 is an X-Y plot representative of optically-based interrogation data obtainable using certain preferred sensor embodiments.

Certain sensors may include structure to optionally, or alternatively, permit optically-based interrogation of particles entrained in a fluid. It should be noted, for purpose of this disclosure, that the term "wavelength" is typically employed not with reference only to a single specific wavelength, but rather to encompass a spread of wavelengths grouped about a characteristic, or representative, wavelength. With reference to FIG. 19, the characteristic wavelength F1 (e.g. excitation wavelength) of a primary radiation source is sufficiently different from the characteristic wavelength F2 of the fluorescence (e.g. emission wavelength) to enable differentiation between the two. Furthermore, the difference between such characteristic wavelengths, or Stokes shift, is desirably sufficiently different to enable, in certain embodiments, including a selective-pass filter element between the radiation source and optical detector effective to block transmission of primary radiation toward the detector, while permitting transmission of the fluorescence through the selective-pass filter to the detector.

Figure 20:
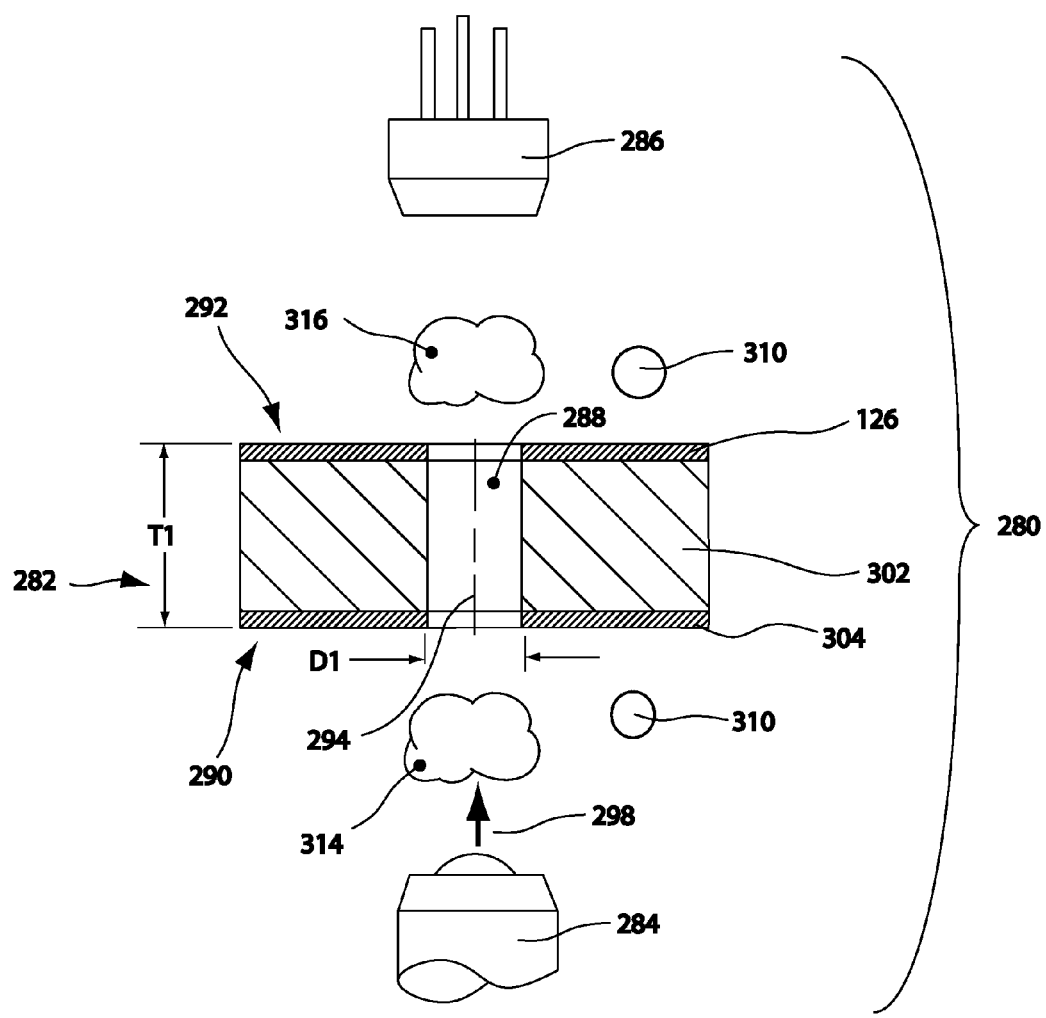
FIG. 20 is a schematic of a cross-section taken through an embodiment illustrating general principles of optically-based operation of certain embodiments of the invention.

A schematic illustrating a generalized operable arrangement of structure employed in embodiments structured according to certain principles of the invention and enabling optically-based interrogation is indicated generally at 280 in FIG. 20. As illustrated, embodiment 280 includes an opaque member, generally indicated at 282, disposed between a radiation source 284 and a radiation detector 286. At least one orifice 288 is disposed in opaque member 282 to provide a flow path between a first side, generally indicated at 290, and a second side, generally indicated at 292. Orifice 288 may be characterized as having a through-axis 294 extending between the first and second sides 290 and 292 of opaque member 282, respectively.

Both of the thickness, T1, of an opaque member and characteristic size, D1, of an orifice 288 are typically sized in agreement with a size of a particle of interest to promote single-file travel of the particle through the opaque member, and to have only one particle inside the orifice at a time. In the case where the apparatus is used to interrogate blood cells, the thickness of the opaque member may typically range between about 10 microns and about 300 microns, with a thickness of about 125 microns being currently preferred. The diameter, or other characteristic size of the orifice in such an embodiment, may range between about 5 and 200 microns, with a diameter of about 60 microns being currently preferred in an embodiment adapted to interrogate blood cells.

An operable opaque member 282 functions, in part, to reduce the quantity of unwanted background radiation, including primary radiation 298 (sometimes also called stimulation radiation) that is emitted by source 284, which is received and detected by radiation detector 286. Primary radiation 298 is illustrated as a vector having a direction. Desirably, substantially all of the primary radiation 298 is prevented from being detected by the radiation detector 286. In any case, operable embodiments are structured to resist saturation of the detector 286 by primary radiation 298. As illustrated in the arrangement depicted in FIG. 20, primary radiation 298 may simply pass through orifice 288 for reception by the radiation detector 286. Therefore, as will be further detailed below, certain embodiments may employ one or more selective radiation filters as a measure to control radiation received by detector 286.

The opaque member 282 illustrated in FIG. 20 includes a core element 302, carrying a first coating 304 disposed on first side 110, and a second coating 306 disposed on second side 112. A workable core 302 for use in detecting small sized particles, such as certain blood cells, can be formed from a thin polymer film, such as PET having a thickness of about 0.005 inches. Such polymer material is substantially permeable to radiation, so one or more coatings, such as either or both of coating 304 and 306, is typically applied to such core material. A workable coating includes a metal or alloy of metals that can be applied as a thin layer, such as by sputtering, vapor deposition, or other well-known technique. Ideally, the metal layer should be about 2-times as thick as the wavelength of the primary radiation, e.g. about 1 µm in one operable embodiment. The resulting metallized film may be essentially impervious to transmission of radiation, except where interrupted by an orifice, such as orifice 288. Aluminum is one metal suitable for application on a core 302 as a coating 304 and/or 306. Of course, it is also within contemplation to alternatively use a bare core element that is, itself, inherently resistant to transmission of radiation. For example, a sheet of metal foil may form an effective opaque member in certain operable embodiments.

The apparatus 280 is configured to urge a plurality of particles 310 into substantially single-file travel through orifice 288. A particle 310 typically passes through an excitation zone as the particle approaches, passes through, and departs from the orifice 288. Of note, the direction of particle-bearing fluid flow may be in either direction through orifice 288. In certain cases, an excitation zone may include the through-channel or tunnel defined by orifice 288. An excitation zone may also include a volume indicated by lower cloud 314, which encompasses a volume in which a particle may reside and be in contact with primary radiation. An excitation zone may further include a volume indicated by upper cloud 316, which also encompasses a volume in which a particle may reside and be in contact with primary radiation.

In certain cases, e.g. where there may be a plurality of orifices, the term "zone" may include a plurality of such distributed zones. However, the appropriate meaning of the term "zone" is believed to be aduceable in context. In the excitation zone, primary radiation 298 causes certain particles to fluoresce, thereby emitting radiation at a different wavelength compared to the primary radiation 298 and in substantially all three-dimensions. The fluorescence radiation emitted by those certain particles may then be detected by the radiation detector 286.

With reference again to FIG. 20, the embodiment 280 may essentially be disposed in a suitably sized container that is divided into two portions by the opaque member. Flow of fluid (and particles entrained in that fluid) through the orifice 288 could be controlled by a difference in pressure between the two divided portions. However, it is typically desired to provide more control over the flow path of particles in the vicinity of the orifice 288 than such an embodiment would permit. For example, a clump of particles disposed near an entrance or exit of the orifice 288 could shield a particle of interest from the primary radiation 298 to the extent that fluorescence does not occur, thereby causing a miscount, or preventing detection of such a shielded particle of interest. Also, clumped or stacked particles could shield fluorescence that is emitted from a particle of interest from contact with the detector, thereby reducing detection accuracy.

Figure 21:
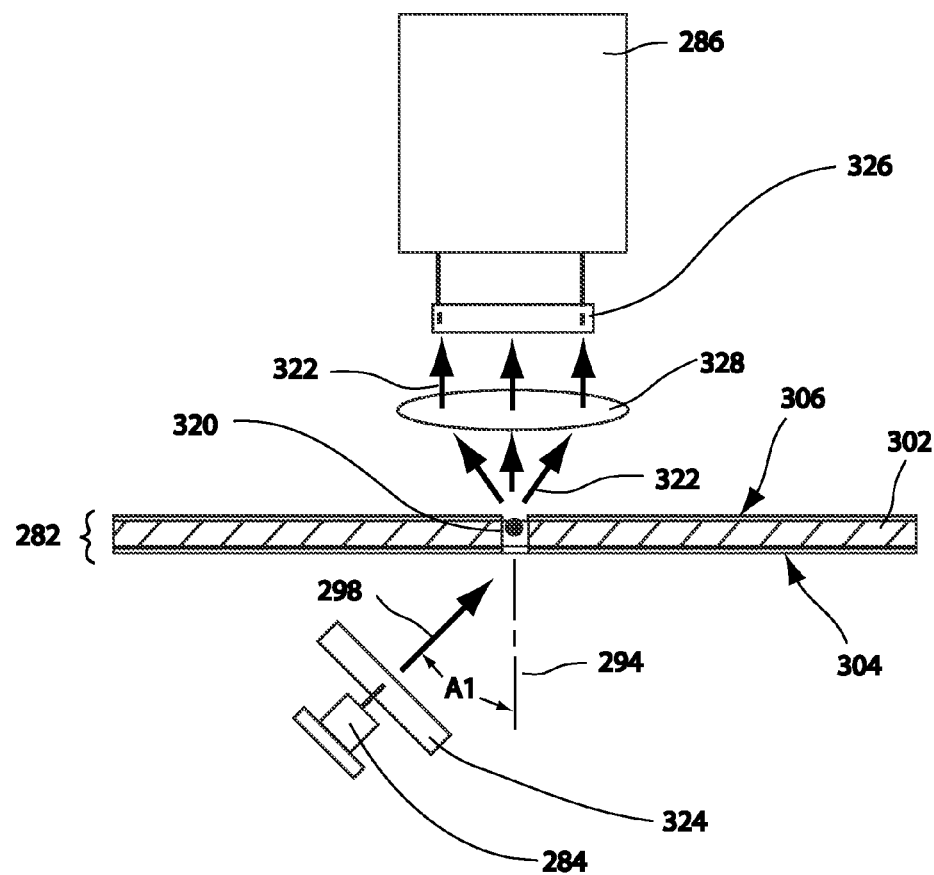
FIG. 21 is a view in elevation of a currently preferred arrangement for certain structure of an operable interrogation platform.

Because fluorescence propagates from a tagged and excited particle of interest in substantially all directions, the primary radiation may be directed to an excitation zone from a side, instead of only from directly below such zone. With reference now to FIG. 21, sometimes it is preferred to apply primary radiation 298 at an angle A1 to axis 114 of orifice 288. In such case, the opaque member 282 may even function substantially as an operable filter to resist direct transmission of primary radiation 298 to a radiation detector 286. As illustrated, radiation vector 298 can be oriented to pass through, or partially into, orifice 288 without being detected by radiation detector 286. However, when a tagged particle 320 is present in an excitation zone (such as orifice 288 as illustrated), the resulting fluorescence 322 may still be detected by the radiation detector 286. While a workable angle A1 may be between 0 and 90 degrees, it is currently preferred for angle A1 to be between about 15 and about 75 degrees for certain operable embodiments.

A radiation source 284 may be formed from a broad spectrum radiation emitter, such as a white light source. In such case, it is typically preferred to include a pre-filter 324 adapted to pass, or transmit, radiation only in a relatively narrow band encompassing the characteristic value required to excite a particular fluorescing agent associated with a particle of interest. It is generally a good idea to limit the quantity of applied radiation 298 that is outside the excitation wavelength to reduce likelihood of undesired saturation of the radiation detector 286, and consequent inability to detect particles of interest.

Certain embodiments apply a red diode laser, and include a short pass filter (after the diode laser) that passes primary light radiation with wavelengths shorter than 640 nm. Such embodiments also may include a band pass filter (prior to the photodetector) with a peak that matches a particular selected fluorescence peak. Commercially available dyes may be obtained having characteristic fluorescent peaks at 660, 694, 725, and 775 nanometers.

With continued reference to FIG. 21, sometimes it is preferred to include a post filter 326 that resists transmission of radiation outside the characteristic wavelength of the fluorescence 322. Such an arrangement helps to avoid false readings indicative of presence of a particle of interest in an excitation zone. Also, to assist in obtaining a strong signal, an optical enhancement, such as a lens 328, can be included to gather fluorescence 322 and direct such radiation toward the radiation detector 286. Illustrated lens 328 may be characterized as a convex focusing lens, and typically is disposed to focus on a point located inside the orifice 288.

Figure 22:
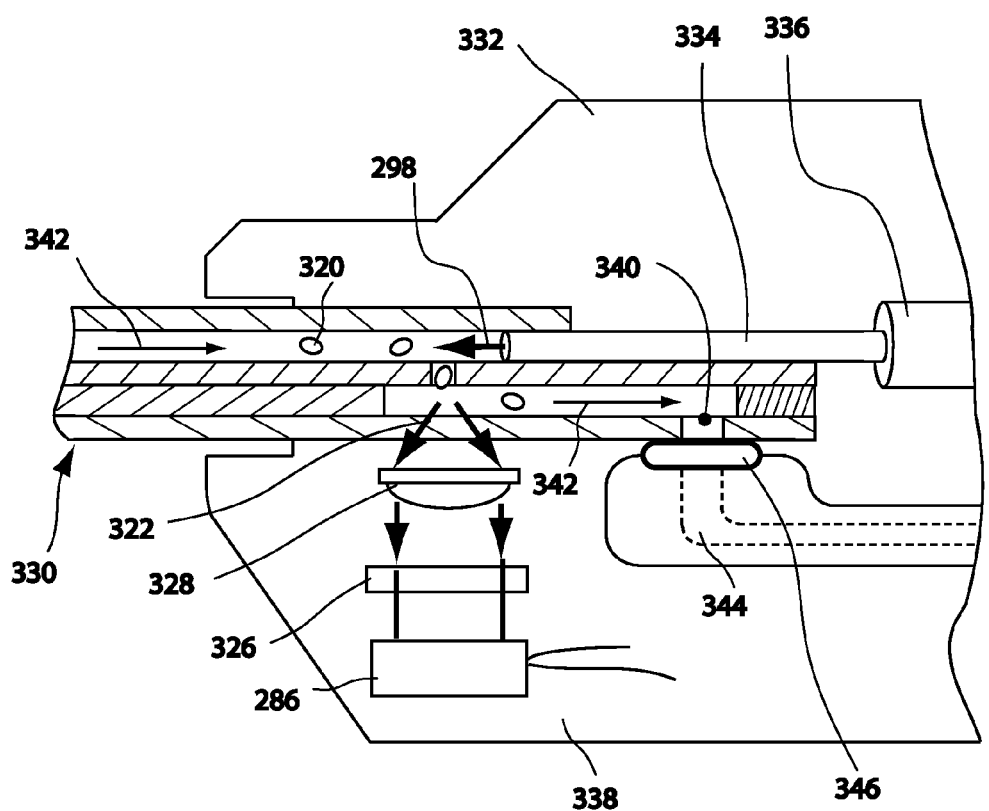
FIG. 22 is a cross-section in elevation, illustrating certain details of a sensor structured as a pipette in association with a portion of an interrogation platform.

With reference now to FIG. 22, an exemplary plumbing arrangement effective to interrogate particles 320 entrained in fluid is indicated generally at 330. The interrogation arrangement 330 is illustrated in an installed position with respect to an interrogation platform 332. A workable interrogation platform 332 may be embodied in various forms, for example as a bench-top device, or as a hand-held instrument, such as a hand-held pipette adapted to extract one or more sample from a bulk container of fluid.

Desirably, coupling the interrogation arrangement 330 to the interrogation platform 332 also places a waveguide, such as light pipe 334 (which, for example, may be a fiber optic cable), into communication with a radiation source. An operable coupling may either be done in "free space" by simply shining the laser into a fiber (or waveguide), or by butt-coupling two fibers together. The radiation source, such as a laser, can be located at virtually any convenient location in the interrogation platform when using the butt-coupling approach.

Figure 23:
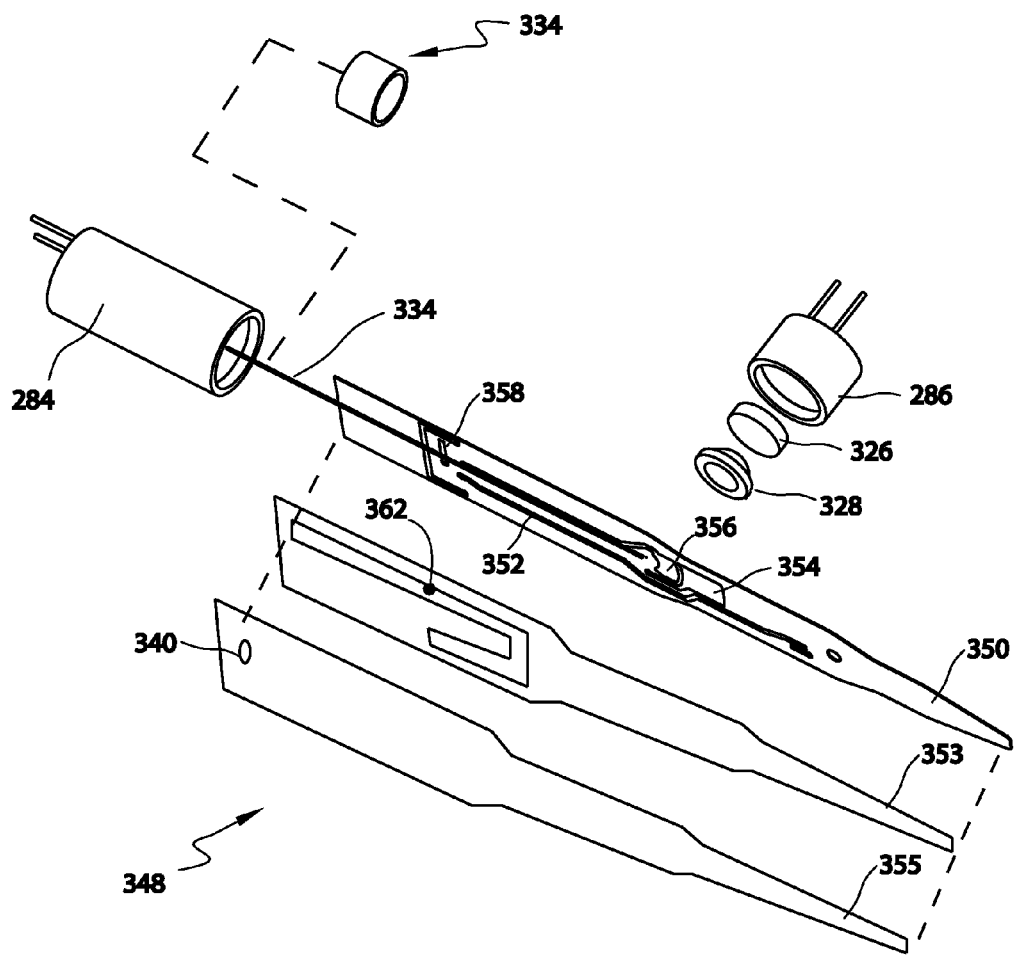
FIG. 23 is a view in perspective, partially exploded, of an electrically instrumented opaque member portion of a sensor structured as a pipette, with the assembly illustrated in operable association with a radiation source and a detector.

As illustrated in FIGS. 22 and 23, an end of light pipe 334 may be engaged by coupling device 336 upon insertion of arrangement 330 into seated engagement in platform 332. Coupling device 336 is structured to orient the end of light pipe 334 in an operable receiving position with respect to radiation provided by a radiation source 284. Therefore, excitation radiation 298 may be impinged onto an interrogation zone, causing emission radiation 322 from particles of interest to propagate toward a radiation detector 286. In an alternative interrogation platform, coupling 336 may place a fiber optic cable (e.g. extending from a more remotely located radiation source) into communication with a light pipe 334, or other waveguide associated with an interrogation arrangement.

Of note, radiation detector 286 may be disposed in proximity to the interrogation site, as suggested by FIG. 22. In such case, wires 338 typically extend from detector 286 to remotely located data collecting devices. Alternatively, radiation detector 286 may be located at a more convenient remote location of the interrogation platform 332, and radiation 322 may be communicated to such remote location by way of a light pipe. As previously indicated, sometimes a focusing element 328, and/or a filter 326 may be included to modify radiation that is transmitted toward detector 286, if desired.

Also as illustrated in FIG. 22, coupling the interrogation arrangement 330 to the platform 332 desirably places a source of suction into fluid communication with flow aperture 340 to cause a desired flow of sample fluid through interrogation arrangement 330, indicated by arrows 342. In the exemplary illustrated embodiment, a source of suction (not illustrated) communicates through passageway 344, which is in sealed communication through an O-ring 346 to aperture 340.

With reference again to FIG. 23, sometimes a plumbing arrangement operable to interrogate particles radiologically may also include structure adapted to interrogate a fluid sample in one or more alternative way. For example, one or more electrodes may be carried by a plumbing arrangement and arranged to permit interrogation of one or more electrical property related to a fluid sample. The partially exploded plumbing arrangement of a disposable embodiment generally indicated at 348 includes an opaque layer 350 that carries a plurality of electrically conductive traces (e.g. trace 352). It should be recognized that layers 353 and 355 are illustrated as being slightly distorted (stretched) to provide clarity as to indicated structure. The conductive traces are configured and arranged to form interrogating electrodes (e.g. 354, 356, 358) that are in electrical communication with connection electrodes or electrically conductive contact pads (e.g. generally indicated at 252 in FIG. 12).

Embodiment 348 exemplifies a multifunction pipette tip that is configured to incorporate both electrical and radiological interrogation of fluid in a single disposable, or sometimes reusable, device. Illustrated embodiment 348 is a multilayer device structured somewhat similarly to a combination of embodiment 130 in FIG. 2 and embodiment 280 in FIG. 20. As pipette tip 348 is coupled to a pipette (not illustrated), light pipe 334 is directed by the internally conic section of coupling 336 effective to align a proximal end of light pipe 334 with a discharge from radiation source 284. A fully installed tip 348 automatically has its light pipe 334 positioned to receive radiation from source 282. Stimulation radiation (light) may then be applied along light pipe 334 to impinge on an interrogation zone associated with the tunnel generally indicated at 228. Further, coupling pipette tip 348 with a pipette also desirably places a vacuum source into communication with flow aperture 340.

Also, surface contact electrodes (disposed on the side facing away for the illustrated embodiment 348) are desirably placed into electrical communication with electrical interrogation circuitry when the pipette tip 348 is seated in an electrically instrumented pipette. Among other uses (such as direct particle counting using measured impedance and the Coulter principle), the electrodes may be arranged to indicate presence of a fluid wave-front at particular locations along a channel, such as a portion of channel 362. In a preferred arrangement, one or more electrode(s) may be arranged to start and stop a test based upon a feedback obtained from the electrode(s).

In general, some sort of feedback signal can be used to indicate a start condition for a test of a fluid sample (e.g. a signal may be generated electrically or optically to detect the fluid wave-front at a known location along a channel). Similarly, some sort of feedback signal can be used to indicate a stop condition for a test on a sample (e.g. electrically or optically detect the wave-front after filling a desired/known volume. Alternatively, a vacuum shut-off signal may be generated by monitoring amperage of the vacuum pump, which may spike when fluid flow terminates by fluid encountering a barrier at the end of a known-volume chamber that resists fluid flow but permits passage of air). Also, the test volume may be substantially controlled by a known quantity of fluid being aspirated into a cassette or cartridge.

With reference still to FIG. 23, an electrode (e.g. 354) may be desirably disposed to indicate the presence of a fluid wave front at the beginning of a length of channel defining a chamber having a known volume corresponding to a desired sample volume size. The signal monitored at electrode 354 may provide a useful start-test signal. A second electrode (e.g. 358) may be disposed at the other end of the known-volume chamber to provide a stop-test signal. A discontinuous change in impedance measured at an electrode (essentially changing from open-circuit to a measurable value as an electrolytic fluid closes the circuit) can be used to indicate arrival of the fluid wave-front. Such start- and stop-signals may be used to advantage to substantially automate data collection during radiological tests of fluid samples.

Elements of a currently preferred sensor arrangement that may be structured as a cassette, or cartridge, are illustrated with reference to FIGS. 24-28. An exemplary such sensor arrangement is structured from a plurality of thin film layers that are stacked and bonded together to form cartridge 370. With reference to FIG. 28, cartridge 370 includes top cap layer 372, top channel layer 374, interrogation layer 376, bottom channel layer 378, and bottom cap layer 380.

The currently preferred top cap layer 372 and bottom cap layer 380 may be made from 0.005" thick transparent polyester film. Workable channel layers 374 and 378 may be made from 0.010" thick double sided acrylic based adhesive. In such case, the center carrier layer may be 0.007" thick polyester with 0.0015" thick adhesive coated on each side. A currently preferred interrogation layer 376 may be made from an assortment of materials, depending upon the intended use for the particular sensor that will be constructed. A clear 0.005" thick polyester film may be used for sensors structured to interrogate impedance measurements only. It is preferred to employ an opaque polyamide film for sensors structured to interrogate impedance and fluorescence (or just fluorescence). The opaque film inherently resists transmission of undesired radiation toward the Stokes shift detection sensor.

Although such is not required, the illustrated cartridge 370 is a two-ended arrangement structured to provide duplicated structure forming first and second sensors on the same removable platform. Such an arrangement permits associating the cassette 370 at a first orientation with an interrogation device, running a first test, then removing and reversing the cassette 370 to interface with the interrogation device at a second orientation to perform a second test. The first and second tests may be the same type of test, performed on different fluid samples. It is within contemplation that the first and second tests may not be the same, and may also be performed on at least a portion of the same fluid sample. For clarity, the duplicated structures included in the second sensor are indicated with a prime. It is within contemplation to provide a multi-ended arrangement providing a further increased number of sensors (e.g. 3, or 4, or more) on the same cassette, or cartridge.

Top cap layer 372 provides a sample loading port 384, a vent 386, and a vacuum application port 388. A plurality of over-size alignments holes 389 are also included. Alignment holes 389 are oversized to provide clearance for other precise alignment structure during assembly of the cartridge 370. Alternative precision alignment structure may be provided for certain layers, such as 372, 374, 378 and 380. Such alternative alignment structure may then be redacted from the finished cassette during a manufacturing step. Also, in certain embodiments, vent ports 386 are not included.

Figure 24:
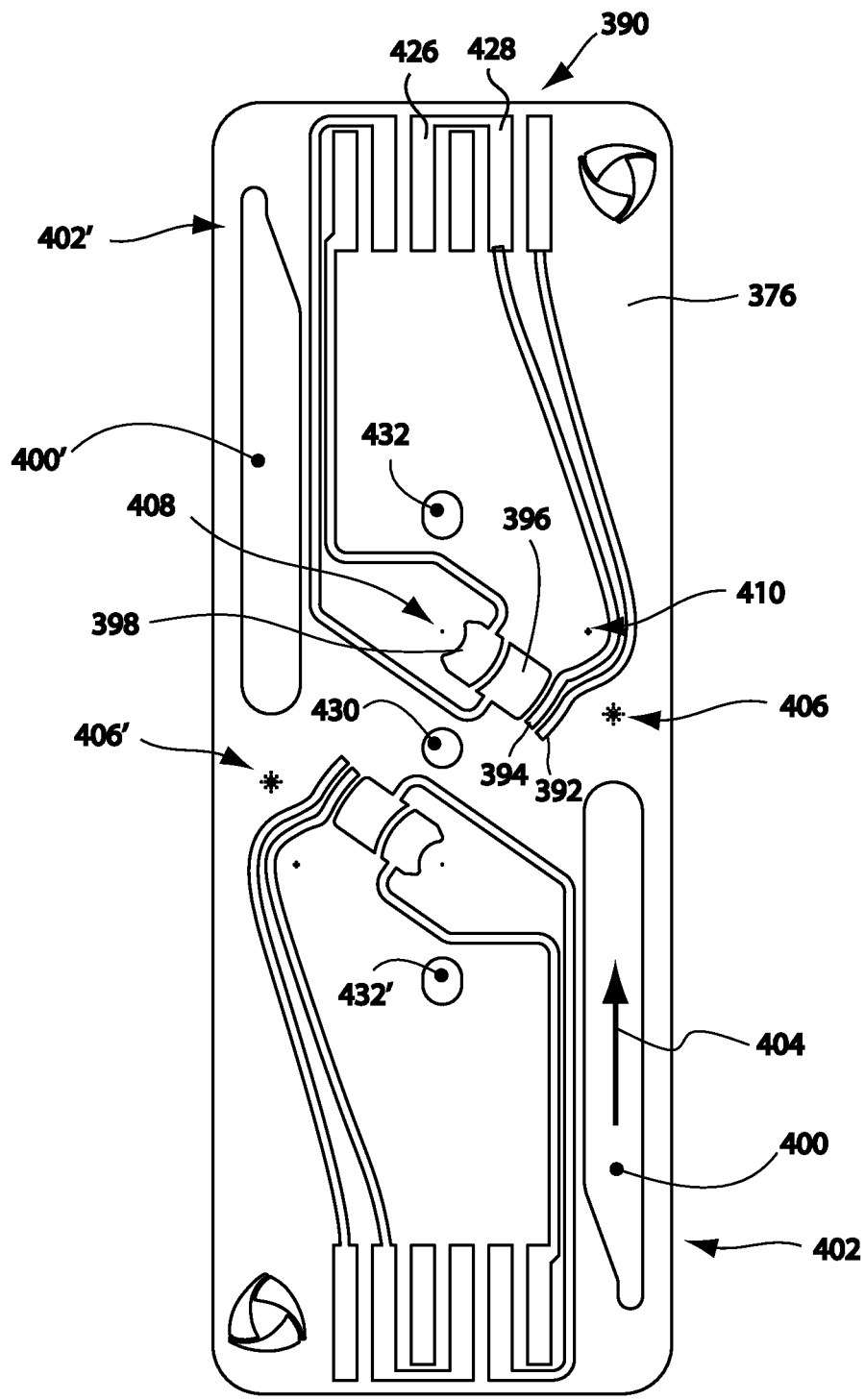
FIG. 24 is a top view of an interrogation layer of a preferred sensor that may be structured as a cassette, or cartridge.

With reference now to FIG. 24, interrogation layer 376 carries a plurality of electrical contact pads, generally indicated at 390. While alternative deposition of conductive material is operable, it is currently preferred to print the contact pads 390 and other conductive traces and structures using electrically conductive ink and a web-based screen printing process that lends itself to mass production.

As illustrated in FIG. 24, a first trigger electrode 392 and a second trigger electrode 394 are disposed upstream of first driving electrode 396 and first detection electrode 398, and may therefore detect a trailing, or fluid flow termination, boundary. Such an arrangement permits electrode 392 and 394 to operate as an electrically-based trigger that is inherently tripped by a fluid flow boundary, and can be used to terminate data collection. For example, impedance can be monitored between electrode 392 and electrode 394. In general, it is desirable for trigger electrodes to be narrow and disposed as close together as possible. The printing capability of the preferred manufacturing method is believed to be the current limit. None-the-less, an electrode area can be fairly small (e.g 0.025"×0.065") and the current printing process can easily maintain a 0.015" spacing between printed electrodes.

With continued reference to FIG. 24, a plurality of apertures and channels are removed from the film forming interrogation layer 376. As illustrated, a partial length channel 400 is disposed to receive a fluid sample for interrogation. The sample is typically loaded at proximal end 402, and flows in the direction indicated by arrow 404, toward debris filter 406. An exemplary debris filter resists passage of undesired particulate matter toward the interrogation aperture 408. It is currently preferred to laser drill a plurality of small apertures in combination to form a sort of screen-like debris filter 406. An additional aperture structure includes fluid exit vent 410. Desirably, exit vent 410 is structured to permit application of vacuum to cause fluid flow through passages in the cartridge 370, and to apply capillary attraction to resist flow of fluid beyond the vent 410, itself.

Figure 25:
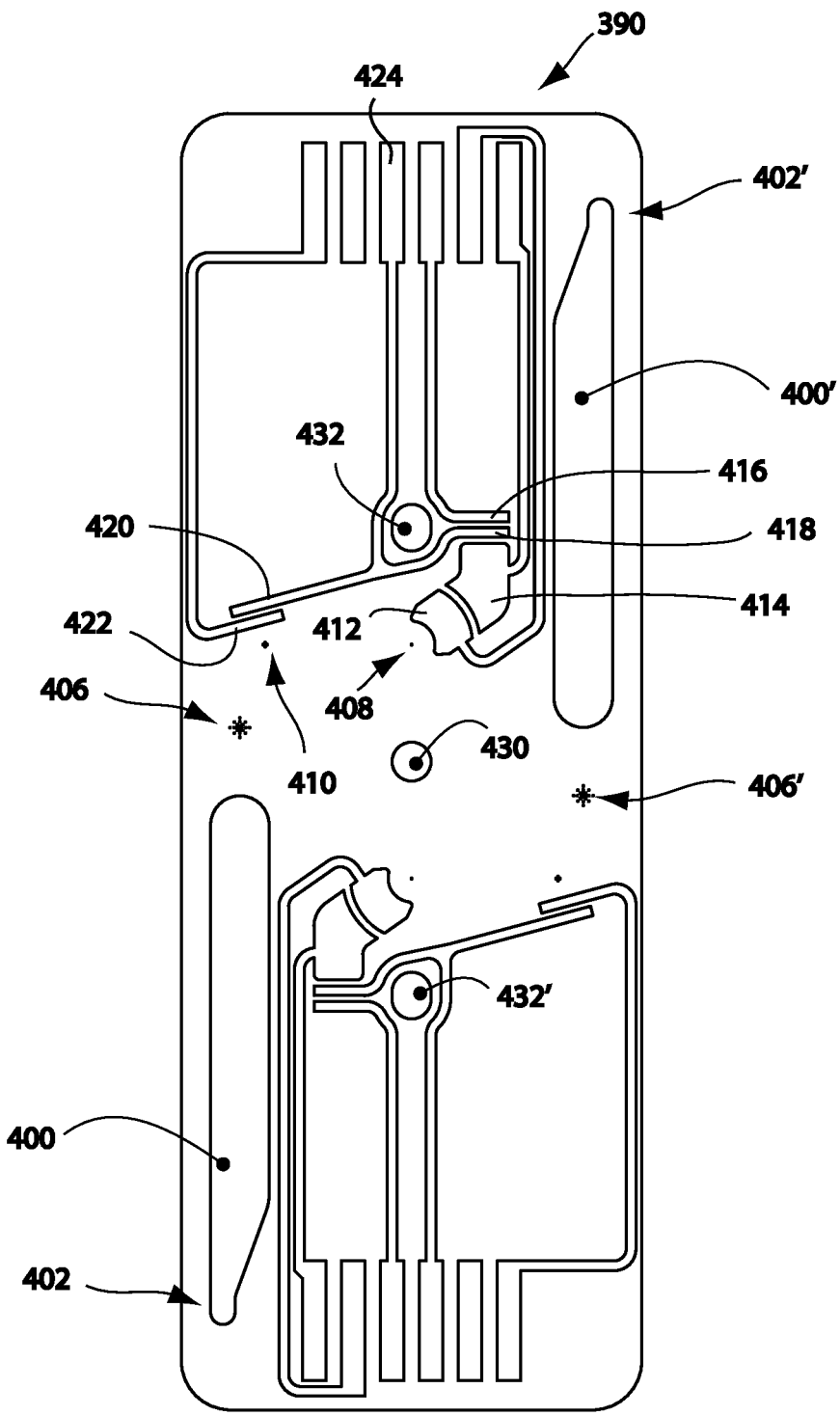
FIG. 25 is a bottom view of the interrogation layer in FIG. 24.

With particular reference to FIG. 25, the other side of interrogation layer 376 includes additional electrical contact pads, generally 390. In the illustrated embodiment, the electrical contact pads 390 disposed on one side are not integral with electrical contact pads 390 on the other side. Electrically conductive traces are configured to provide a second interrogation electrode 412 and a second driving electrode 414.

Still with reference to FIG. 25, a third trigger electrode 416 and a fourth trigger electrode 418 are disposed down stream of second detection electrode 412 and second driving electrode 414 and may therefore detect a fluid flow arrival boundary. Such an arrangement permits trigger electrode 416 and trigger electrode 418 to operate as an electrically-based trigger that is inherently tripped by a fluid flow boundary, and can be used to begin data collection during the test of a fluid sample.

A fifth trigger electrode 420 and a sixth trigger electrode 422 are also illustrated in FIG. 25 as being disposed down stream of second detection electrode 412 and second driving electrode 414 and may therefore cooperate to detect a fluid flow arrival boundary at a second location. This third trigger is disposed near the vent aperture 410. Such an arrangement permits electrode 420 and 422 to operate as an electrically-based trigger that can be used to detect the "end of test" for a fluid sample when using the known volume method with respect to the volume in channel 442.

For convenience, electrode surface contact pad 424 is in electrical communication with both of electrode 418 and 420, and can therefore be used to apply a common reference signal, such as ground. On the other side of layer 376, electrical contact pads 426 and 428 are in electrical communication and may be used in a continuity check to verify proper insertion of a sensor into engagement in a preferred interrogation device. It should be noted that certain sensors may be constructed having a different number of driving, detecting, verification, and/or trigger electrodes, or even none.

Layer 376 also includes a plurality of alignment apertures. Alignment aperture 430 is common to alignment structure used for both ends of the cartridge 370, and imposes an X-Y location at a known reference spot on the cartridge 370 with respect to a currently preferred interrogation device. Alignment slot 432 imposes substantially only a rotational orientation of an installed cartridge 370 with respect to that X-Y location. Desirably, one of the apertures 430, 432 is slotted, and the other is not. Such an arrangement is effective to provide a complete rigid body constraint in a plane, and helps to avoid binding of the cassette during its installation into, or removal from, an interrogation device. The radius of illustrated round alignment aperture 430 is 0.050". The distance between the radii of alignment slot 432 is 0.025" and the radii are 0.050". Cooperating alignment pins in the preferred interrogation device have diameters of 0.1000", and the pins are precision ground to a tolerance of ±0.0001". Planar orientation of the cartridge is typically enforced by other clamping structure associated with the preferred interrogation device.

Figure 26:
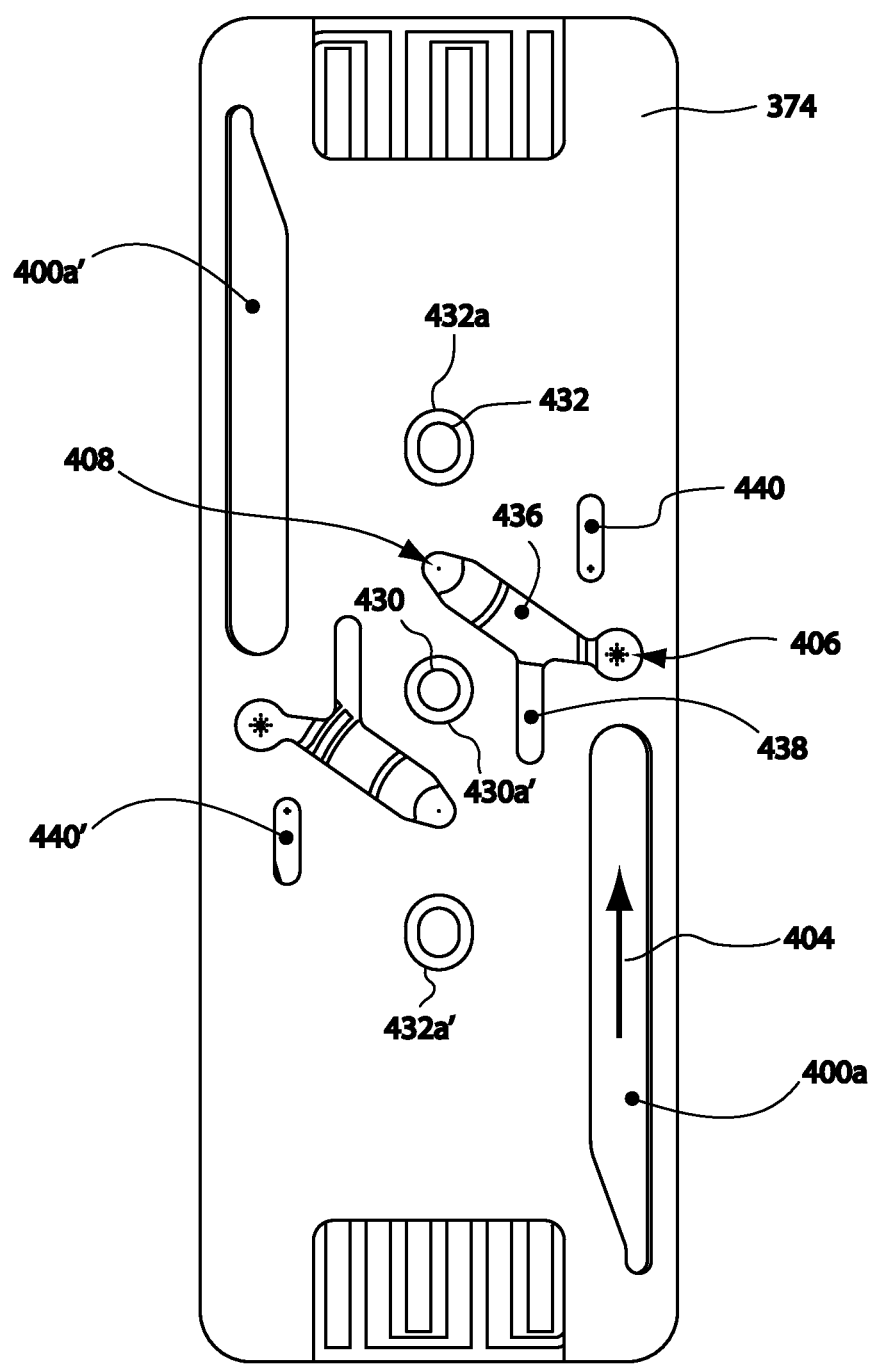
FIG. 26 is a top view of the interrogation layer in FIG. 24, with a channel layer also installed.

With reference now to FIG. 26, top channel layer 374 includes a plurality of channel structures. Partial-length fluid receiving channel 400a cooperates with channel 400 in layer 376 to permit introduced sample fluid to flow in the direction indicated by arrow 404. Bridge channel 436 transports fluid from debris filter 406 toward interrogation aperture 408. An optional dogleg channel portion 438 may communicate to an optional vent 386 (see FIG. 28) at the top of the cartridge 370, and facilitates loading a fluid sample into the cartridge 370. Buffer channel 440 communicates from exit vent 410 toward a vacuum port 388 (see FIG. 28) on top of the cartridge 370. Along with over-size apertures 389, alignment apertures 430a and 432a are also pulled back during a manufacture step to avoid causing a potential structural interference with respect to alignment apertures 430 and 432 disposed in penetration though the interrogation layer.

Figure 27:
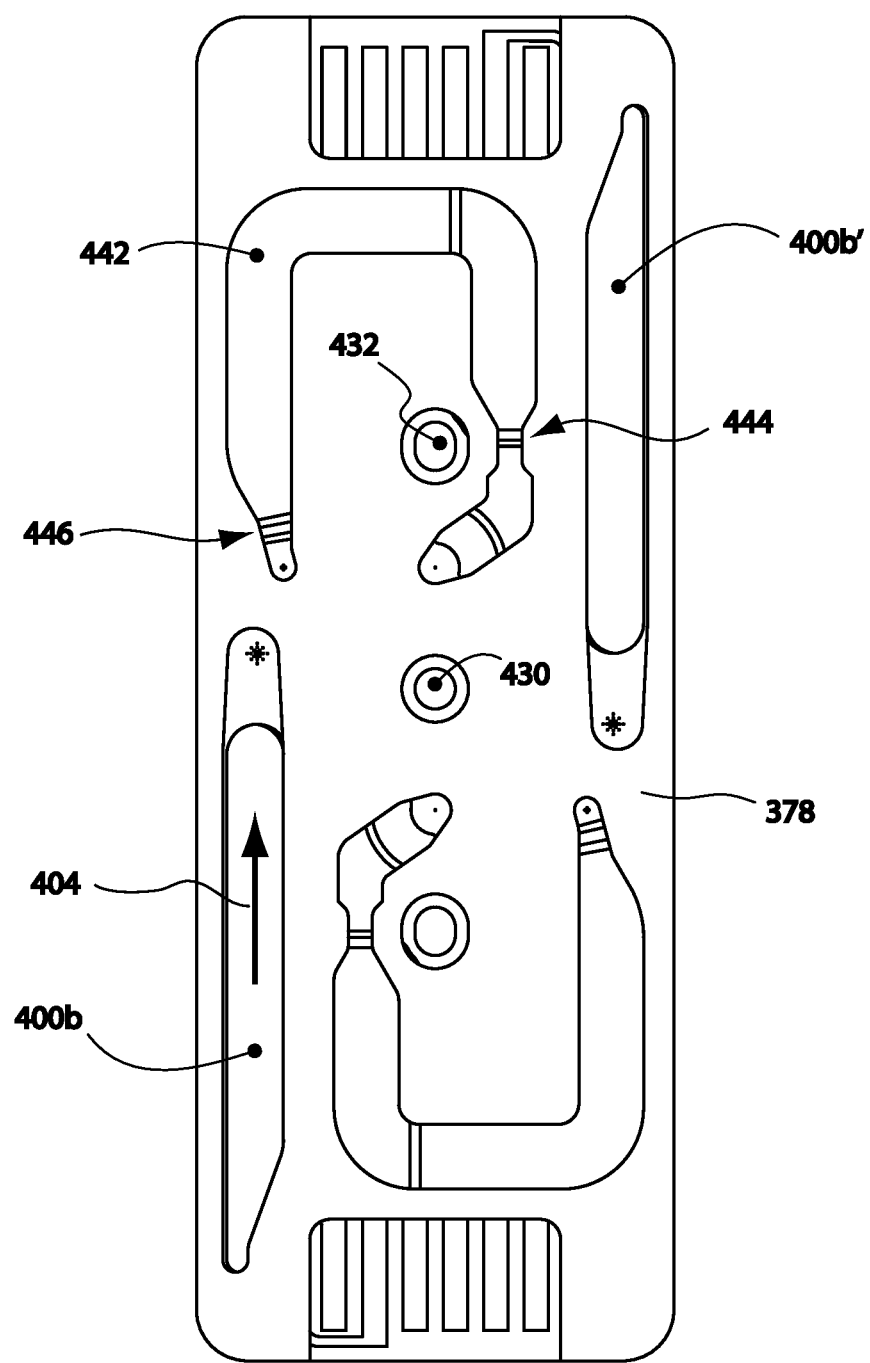
FIG. 27 is a bottom view of an interrogation layer similar to that illustrated in FIG. 24, with a channel layer also installed.
Figure 28:
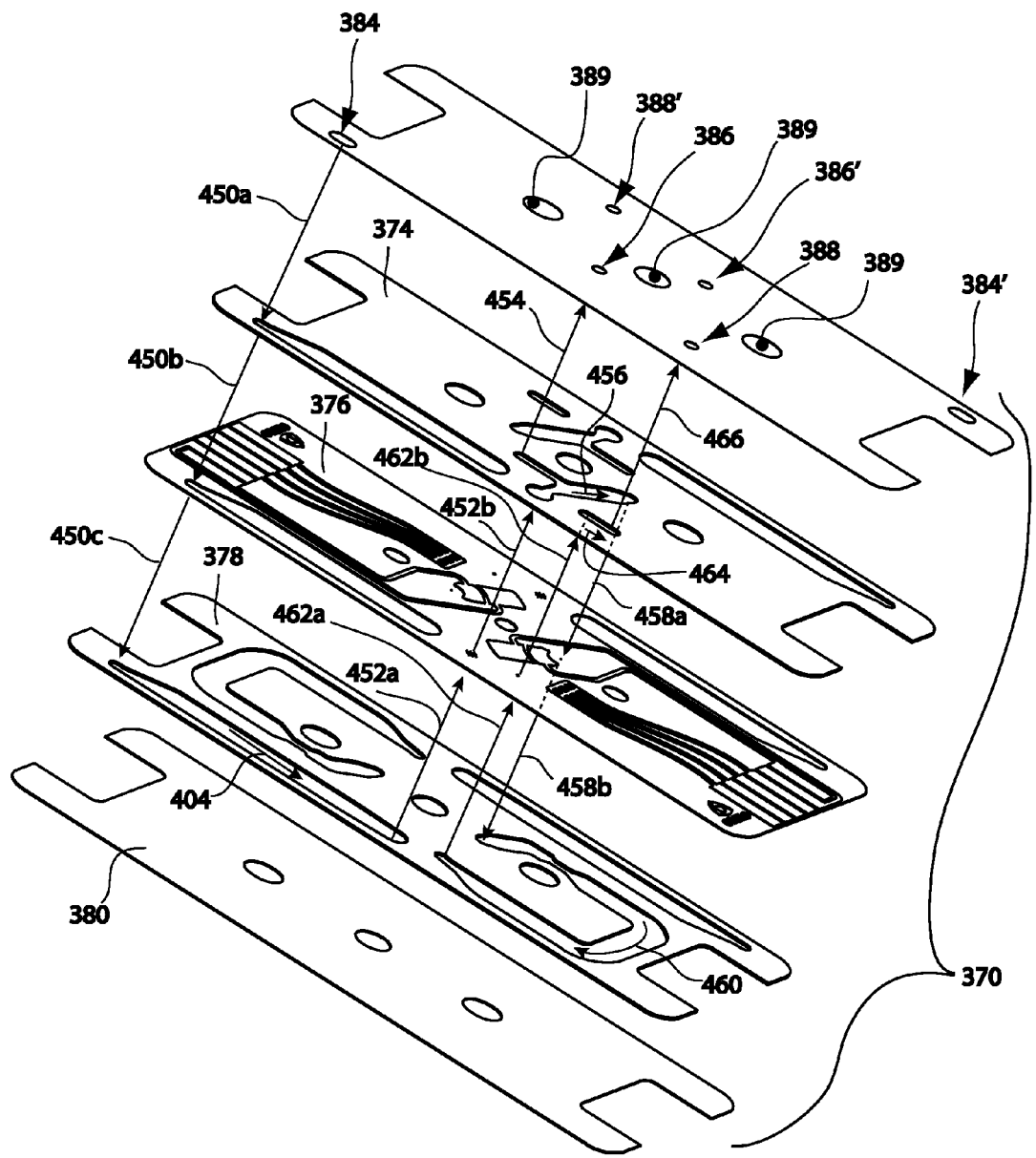
FIG. 28 is an exploded view in perspective of a sensor structured as a cassette and including the interrogation layer in FIG. 24.

With reference now to FIG. 27, bottom channel layer 378 carries full-length sample receiving channel 400b. Channel 400b communicates introduced fluid underneath layer 376 to the bottom of debris filter 406. Channel 442 receive fluid downstream of interrogation aperture 408. In certain embodiments, a first electrically-based trigger, generally indicated at 444, is disposed near one end of the chamber formed by channel 442. A workable trigger may be formed between two dedicated electrodes, or sometimes between one dedicated electrode and a shared electrode. Illustrated trigger 444 in FIG. 27 is formed between electrodes 414 and 418 (see FIG. 25). A trigger at a location such as trigger 444 is operable as a "start" trigger, to begin collection of data during an interrogation of a fluid sample. It has been determined that a single impedance-detecting electrode, such as 418, cooperating with a sink electrode 414 is more reliable than a cooperating dedicated pair of electrodes (e.g. 414 and 416, FIG. 35) disposed in very close association with a sink electrode such as 414.

A second electrically-based trigger, generally 446, may be disposed spaced apart from trigger 444 by a known volume provided by channel 442. Illustrated trigger 446 is formed by electrodes 420 and 422 (see FIG. 25). In certain cases, a second known volume may be defined by channel and aperture structure disposed between trigger 444 and an upstream trigger, such as may be formed between electrodes 292 and 294 (see FIG. 24).

Known volumetric trigger spacing and collection of data signals including a common time component or base, permit: starting and stopping test data collection; control for application of vacuum; confirmation of processing a desired sample volume; and calculation of volumetric rate of processing, among other attributes.

With reference again to FIG. 28, the fluid flow path will now be described. In one type of test, a sample is typically introduced to sample loading port 384 using a pipette instrument to accurately dispense a desired test volume, or sometimes a surplus volume. Entering fluid flow is represented by arrows 450a, 450b and 450c. Sample fluid then flows along a channel formed by channel portions 400, 400a, and 400b in the direction indicated by arrow 404. As indicated by arrows 452a and 452b, fluid flow through debris filter 406 to channel 436. Air may be passed out aperture 386, as indicated by arrow 454. During a test, fluid flows along channel 436 in the direction indicated by arrow 456. Fluid then flows through interrogation aperture 408 as indicated by partially hidden arrows 458a and 458b. Fluid flow in channel 442 is indicated by arrow 460. Fluid then flows through vent 410 as indicated by arrows 462a and 462b. Fluid then flows along channel 440 in layer 374, in the direction indicated by arrow 464, before potentially exiting vacuum port 388, indicated by arrow 466. In certain cases, channel 440 may provide a buffer to resist escape of fluid from a cartridge 370.

Typically, an Excimer laser is used to form the interrogation apertures 408 and alignment apertures 430 and 432. A DPSS laser is generally used to form all of the other channel and aperture structure (filters, vents, channels, etc.). The excimer can cut the currently preferred 55 μm diameter interrogation aperture 408 within ±2 microns. Repeatability of the DPSS is more like plus/minus 5 microns. The large alignment holes 430, 432 are manufactured (laser cut) with extreme precision relative to the laser drilled interrogation aperture 108. Use of the more accurate laser allows the interrogation aperture 408 to be mechanically aligned, from cassette to cassette, to the laser beam of a cooperating docking station of a preferred interrogation device with an accuracy of about 20 μm to 50 μm. Here, "accuracy" means that the center of the aperture is disposed within a certain radius of the theoretical centerline of an interrogation zone provided by a cooperatingly structured interrogation device.

Figure 29:
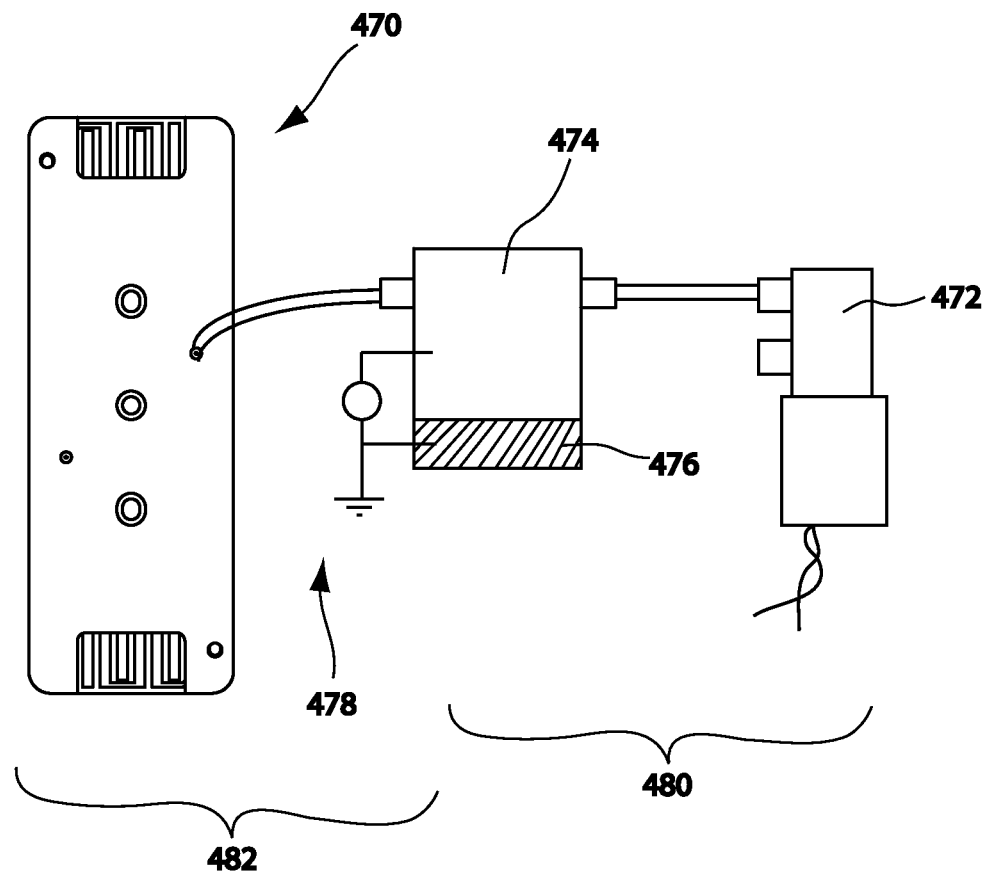
FIG. 29 is a top view of a workable test arrangement including a vacuum source to urge fluid movement through a sensor.

With reference now to FIG. 29, it is within contemplation to use a single sensor a plurality of times. For example, a single sensor, generally indicated at 470, can be used to process a plurality of similar, or different, fluid samples in series. Sensor 470 may be a double-ended sensor as illustrated, or a single-ended sensor, as desired. In any case, a source of vacuum, such as vacuum pump 472, may be applied to a container in which to receive a quantity of fluid samples and potential cleaning flushes between tests. Suction from the container may be applied to the sensor 470 to effect a test, and the fluid sample (and optional flush fluid) may then be extracted from the sensor 470 for storage in the container 474. Workable cleaning/flushing fluids include distilled water, water with detergents, saline, and low bleach concentration in water. In certain cases, a gas, such as air, may be used as an operable cleaning fluid. The level of stored fluid 476 can be monitored by a level control system, generally 478. An operable control system may include a simple float switch, or an electrical impedance sensing circuit. It is alternatively within contemplation to use an optically-based monitoring system for level control, or simply to keep track of the individual sample volume(s) and number of tests performed since the holding chamber was emptied or replaced. A holding chamber 474 may be structured as a portion of an interrogation device, generally 480. Alternatively, storage container 474 may be included as a portion of an alternative sensor 482.

Figure 30:
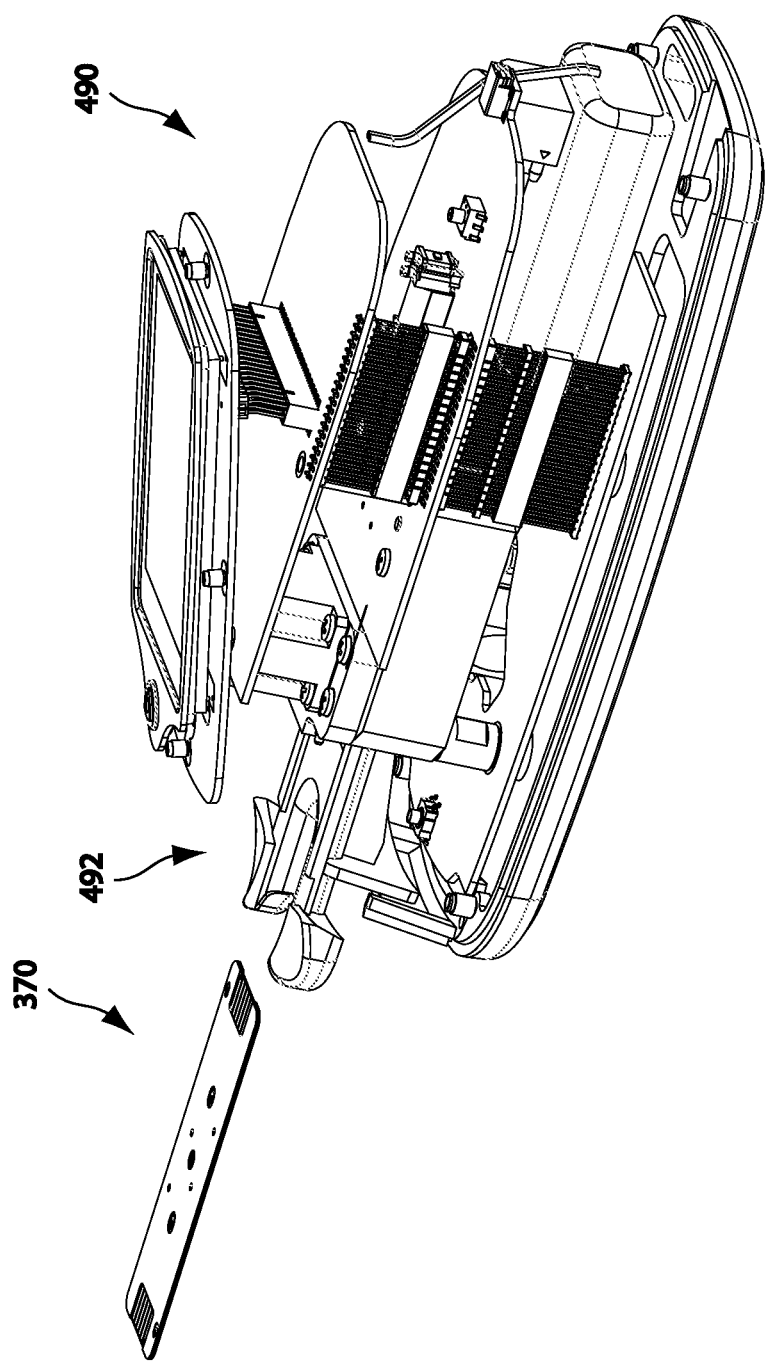
FIG. 30 is a view in perspective of a currently preferred sensor poised for docking with an interrogation platform.

FIGS. 30-32 illustrate one currently preferred interrogation device, generally 490, for use with certain preferred sensor arrangements structured according to certain principles of the instant invention. In FIG. 30, a representative sensor arrangement 370 is ready to load into the device 490. Cassette 370 is received in entrance structure 492, which facilitates alignment of the cassette, and orients the cassette 370 in a plane. Alignment pins 494 enforce an X-Y position on an installed cassette 370 and also a rotational relationship of the cassette 370 with respect to that X-Y position. Such alignment urges the interrogation aperture 408 into operable alignment with an applied source of radiation and with respect to optical detector 496 effective to detect Stokes' shift phenomena that may occur in the interrogation zone. Electrical contact prongs (e.g. edge connectors) and appropriate electronic devices, may be included in a device 490 to permit electrically-based particle interrogation, as well, or instead. The vacuum ports are desirably located near the alignment pins so the cassette only needs to be clamped in one location. The clamping step preferably makes the vacuum seal and accurately positions the interrogation orifice.

Figure 33:
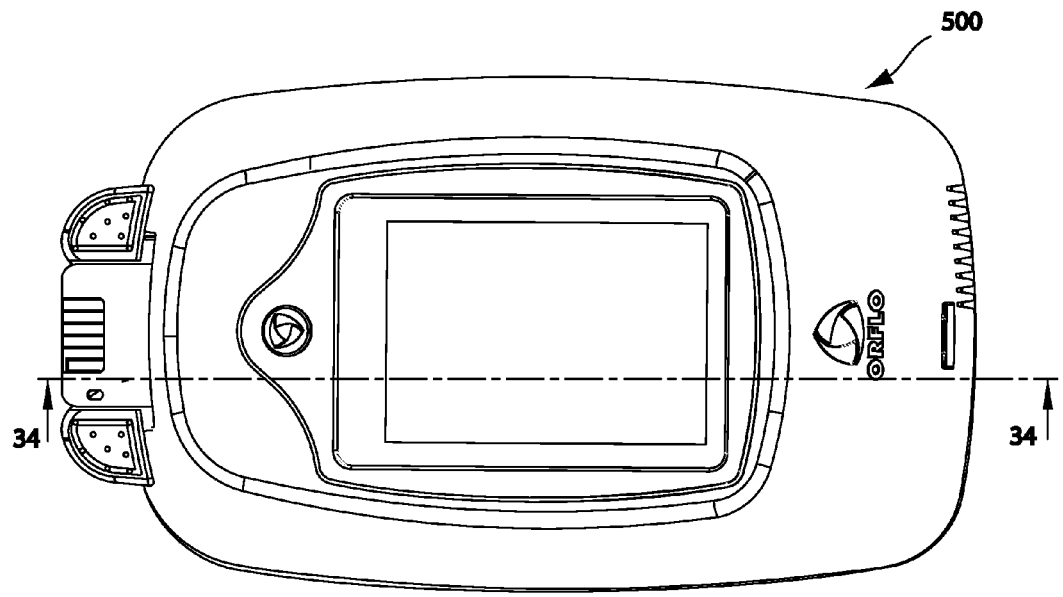
FIG. 33 is a top view of an alternative interrogation platform
Figure 34:
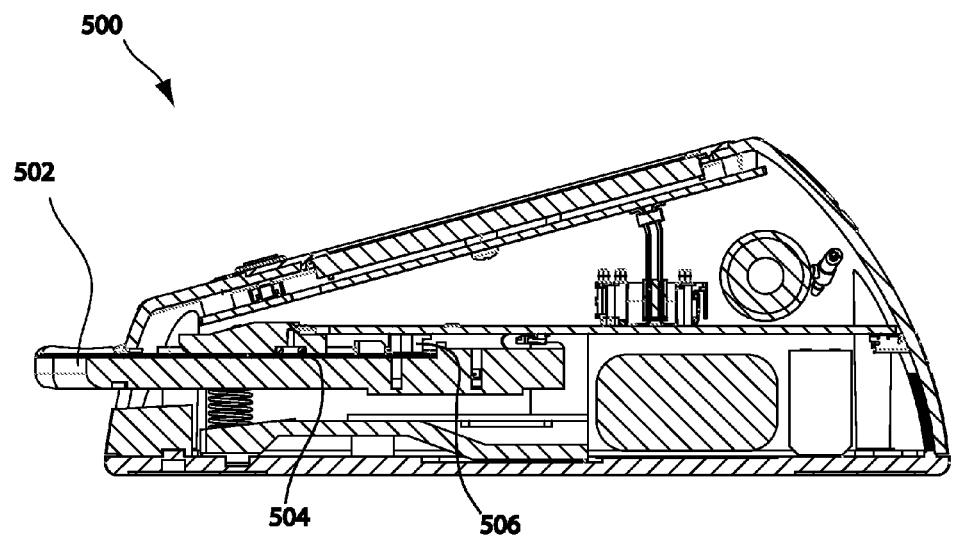
FIG. 34 is a cross-section view in elevation taken through section 34-34 in FIG. 33 and looking in the direction of the arrows.

FIGS. 33 and 34 illustrate an alternative interrogation platform, or device, generally at 500. Installation of a test cassette 502 causes a clamping force between the cassette 502 and a vent seal, such as O-ring 504, as well as places a vacuum source into communication with a vacuum application port 388. An air resistant connection may be effected at the vacuum port with an O-ring, as well. Electrical contact pads 390 of an installed cassette 502 are inherently placed into electrical communication with appropriate pins of electrical connectors, such as edge connector 506. Of course, such electrical connectors are disposed for contact with electrodes 390 that are carried on either of, or both of, top and bottom of an installed cassette 502, as the case may be.

Figure 35:
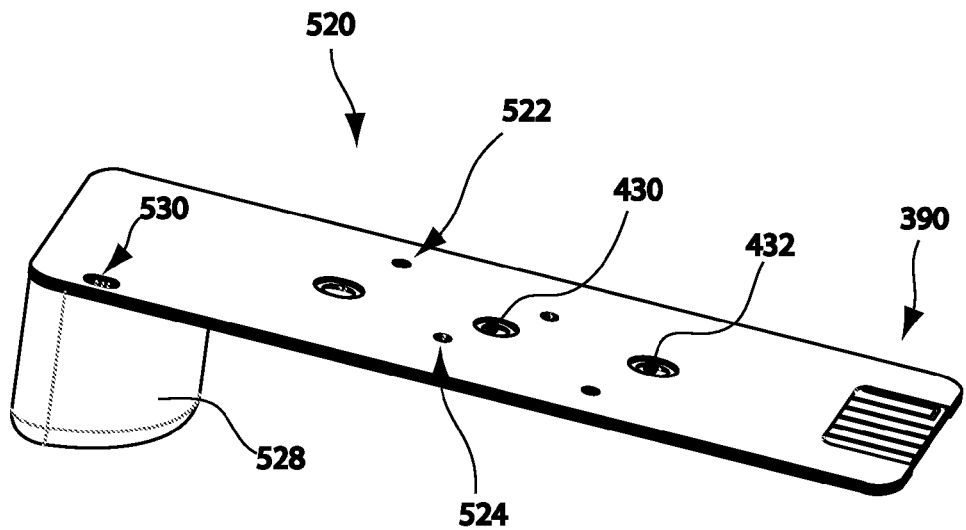
FIG. 35 a view in perspective of an alternative sensor embodiment adapted for serial processing of a plurality of fluid samples.

With reference now to FIG. 35, the particle sensor embodied in the test cassette generally indicated at 520 is adapted to permit interrogating a plurality of discrete fluid samples in series. Each successive fluid sample may be input to cassette 520 by way of pipetting a dose of fluid into sample port 522. Desirably, successive fluid samples may be input into the cassette 520 without removing the cassette from an interrogation device between samples. A vent 524 may be provided to facilitate loading each fluid sample into cassette 520. Alignment apertures 430 and 432 help to align the cassette 520 upon installation in an interrogation device, such as device 490 or device 500. Certain cassettes 520 may include electrode contact pads 390, and generally be structured similar to the cartridge 370. One difference, however, is the reservoir 528, which permits storing a plurality of interrogated fluid sample on-board the cassette 520. Desirably, reservoir 528 is sized to contain a plurality of fluid samples and also a plurality of doses of cassette-cleaning flush fluids that may be vacuumed through the cassette 520 between each interrogated fluid sample. Vacuum is applied at vacuum port 530, and samples (and flush or cleaning fluids, if used) collect inside reservoir 528. One embodiment of a cassette is structured to perform at least 10 tests. Providing for about 75 µl fluid sample per test (times 10), plus about 50 µl of cleaner fluid in between test samples (times 9) requires a reservoir 528 to accommodate at least about 1.25 ml total fluid volume. A cassette 520 may be structured to permit interrogation of fluid samples using Stokes' Shift phenomena, and/or by monitoring an electrical phenomena, such as the Coulter principle, or difference between an open-circuit and a closed-circuit.

In one method of use of a preferred embodiment, a sensor structured as a cassette is loaded into registration, at a first orientation, in an interrogation device. A fluid sample may be loaded into the cassette either before, or after, installing the cassette in the interrogation device. The fluid sample is urged to flow through the cassette, typically by application of a vacuum at an end of a lumen opposite the sample entrance port.

Sometimes, a known volume of fluid is transferred to the cassette for a given sample. In certain such cases, the fluid sample may be urged to flow through the cassette, and one or more triggers may indicate a "start" and/or "stop" for collection of test data. For example, impedance at a first location along a lumen (e.g. downstream of fully wetted interrogation electrodes or a Stokes' shift interrogation zone) may be monitored, and when a fluid wave front is detected, data collection may be started. Data collection may be stopped when a fluid wave front is detected at a second location (e.g. upstream of fully wetted interrogation electrodes or a Stokes' shift interrogation zone). The known volume of the lumen between the first and second locations may then be subtracted from the transferred volume of fluid to calculate a volume of interrogated fluid.

For example, in one currently preferred arrangement, the user just pipettes 75 uL of sample into the receiving channel of a cassette. It helps to tilt the cassette to have gravity assist the filling. The cassette is installed in registration in an interrogation device, and vacuum is applied. Counting begins when the approaching fluid wave front is detected at a start trigger location, e.g. disposed downstream of the interrogation aperture and all driving and detecting electrodes. Counting is stopped, and vacuum removed, once a stop trigger detects the trailing fluid wave front. In a preferred cassette, about 25 µl of fluid is disposed in the volume between the start and stop triggers, so a 50 µl sample is interrogated.

In steps of another method, data collection may be terminated when a fluid wave front is detected at a trigger location spaced apart downstream of the first location by a known volume (at a third location). Sometimes, the trigger at the third location may be used as a redundant signal, or safety signal, to resist undesired escape of fluid from confinement inside the cassette. For example, a safety signal can be used to terminate application of vacuum to stop flow of fluid through the cassette.

In certain cases, after a first fluid sample is processed, the cassette is removed, and reinstalled in registration in the interrogation device at a second orientation to process a subsequent second fluid sample. Sometimes, certain two-ended cassettes are rotated by 180 degrees between such first and second fluid samples. In certain alternative cases, a vacuum is used to pull all fluid of one fluid sample past the interrogation zone and/or electrodes, and a new sample may subsequently be introduced to a cassette. Successive fluid samples are generally stored in a container, which may be carried by a cassette, or associated with an interrogation device. In certain situations, it is desirable for the cassette to remain installed in the interrogation device between samples, although such is not required. It is further within contemplation to flush, or clean, a lumen through a cassette by drawing a quantity of cleaning fluid (potentially including a gaseous fluid, such as air) through the cassette between serial interrogation of fluid samples.

It is desirable to monitor the "health" of a cassette, to verify that the interrogation zone is not compromised, i.e. clogged by particulate matter. One way to do so includes use of a differential +15/−15V constant current stimulus (e.g. apply the −15V on a "sink" electrode) and a differential measurement technique across the interrogation aperture. Therefore, the measured voltage across the aperture is close to zero when the sensor is filled with conductive media. When a cell passes through the aperture, the measured voltage increases momentarily. If a blockage occurs, the voltage usually rails to +15V (momentarily). It generally settles back down shortly thereafter, because the interrogation device is AC coupled. It is also preferred to measure the total time of the counting and if it exceeds some amount (like one minute), to stop the test and report "aperture block".

While the invention has been described in particular with reference to certain illustrated embodiments, such is not intended to limit the scope of the invention. The present invention may be embodied in other specific forms without departing from its spirit or essential characteristics. The described embodiments are to be considered as illustrative and not restrictive. The scope of the invention is, therefore, indicated by the appended claims rather than by the foregoing description. All changes which come within the meaning and range of equivalency of the claims are to be embraced within their scope.

What is claimed is:

1. A microfluidic sensor, comprising:
   a plurality of stacked thin film substantially planar layers forming a cassette providing structure defining a fluid path disposed inside said sensor, said path comprising:
      a first portion disposed parallel to, and within, said layers;
      a second portion provided by a tunnel passing through an interrogation layer, a constriction in said tunnel being sized to urge particles entrained in a carrier fluid into substantially single-file travel through a particle interrogation zone; and
      a third portion disposed parallel to, and within, said layers, said first portion and said third portion being disposed on opposite sides of said particle interrogation zone; and
   a waste reservoir associated with said fluid path and structured to receive a plurality of individual and serially interrogated fluid samples.

2. The sensor according to claim 1, wherein:
   said waste reservoir is associated with an interrogation device.

3. The sensor according to claim 1, wherein:
   said cassette is structured for insertion into an interrogation device at a first optical interrogation orientation to permit running a first test, then to permit withdrawal and rotation of said cassette to a second optical interrogation orientation that is different from said first orientation for reinsertion of said cassette to permit running a second test.

4. The sensor according to claim 1, wherein:
   certain of said layers carry one or more electrode to dispose a plurality of electrodes in a 3-dimensional array in space; and
   said cassette is structured for insertion into an interrogation device at a first electrical connection orientation to permit running a first test, then to permit withdrawal and rotation of said cassette to a second electrical connection orientation that is different from said first orientation for reinsertion of said cassette to permit running a second test.

5. The sensor according to claim 1, further comprising:
   means to detect a level of fluid in said reservoir.

6. The sensor according to claim 5, wherein:
   said waste reservoir is carried by said sensor.

7. The sensor according to claim 1, further comprising:
   alignment hole structure disposed relative to said second portion effective to facilitate precision orienting said second portion of an optically-based testing cassette when said alignment hole structure is installed in registration with alignment pin structure of a cooperatingly structured interrogation device.

8. The sensor according to claim 7, wherein:
   said alignment hole structure comprises:
      a first aperture structured to define an X-Y position of a cassette at an installed position in, and with respect to, a cooperatingly structured interrogation device; and
      a second aperture structured to interact with cooperating structure of said interrogation device to enforce substantially only a rotational aspect of said cassette with respect to said X-Y position.

9. The sensor according to claim 1, wherein:
   certain of said layers carry one or more electrode to dispose a plurality of electrodes in a 3-dimensional array in space; said electrodes comprising:
      a first stimulated electrode disposed for contact with fluid in said first portion;
      a second stimulated electrode disposed for contact with fluid in said third portion;
      a first interrogation electrode disposed for contact with fluid between said first stimulated electrode and said second stimulated electrode; and
      a first trigger electrode arrangement operable to indicate a stop signal based upon detection of a fluid boundary, said first trigger electrode arrangement comprising a dedicated electrode disposed upstream of said second portion.

10. The sensor according to claim 9, further comprising:
   a second trigger electrode arrangement operable to indicate a start signal based upon detection of a fluid boundary, said second trigger electrode arrangement comprising a dedicated electrode disposed downstream of said second portion and spaced apart from said first trigger electrode arrangement by a length of lumen defining a known volume.

11. The sensor according to claim 9, further comprising:
   a second trigger electrode arrangement operable to indicate a start signal based upon detection of a fluid boundary, said second trigger electrode arrangement comprising a dedicated electrode disposed downstream of said second portion; and
   a third trigger electrode arrangement operable to indicate a stop signal based upon detection of a fluid boundary, said third trigger electrode arrangement comprising a dedicated electrode disposed downstream of said second portion and spaced apart from said second trigger electrode arrangement by a length of lumen defining a known volume.

12. A method for manufacturing a multi-layer microfluidic sensor structured according to claim 1, comprising:
   forming a first fluid-flow channel in a first layer of thin film, said first fluid-flow channel being configured to permit fluid flow in a direction generally parallel to said first layer;
   forming a second fluid-flow channel passing through a second layer of thin film to create an interrogation layer, said second fluid-flow channel being sized to urge single-file travel therethrough of particles entrained in a carrier fluid;

forming a third fluid-flow channel in a third layer of thin film, said third fluid-flow channel being configured to permit fluid flow in a direction generally parallel to said third layer, said first, second, and third fluid-flow channel being configured as individual portions of a first lumen extending through said sensor;

forming a plurality of alignment holes in penetration through said interrogation layer and disposed with sufficient precision relative to said second fluid-flow channel such that installation of two of said alignment holes in registration with respective locating pins of a cooperatingly structured interrogation device is effective to dispose said second fluid-flow channel at an interrogation location of said interrogation device within an accuracy of about 50 µm.

13. The method according to claim 12, further comprising:

forming a fourth fluid-flow channel in said first layer of thin film, said fourth fluid-flow channel being configured to permit fluid flow in a direction generally parallel to said first layer;

forming a fifth fluid-flow channel passing through said second layer of thin film, said fifth fluid-flow channel being sized to urge single-file travel therethrough of particles entrained in a carrier fluid;

forming a sixth fluid-flow channel in said third layer of thin film, said sixth fluid-flow channel being configured to permit fluid flow in a direction generally parallel to said third layer, said forth, fifth, and sixth fluid-flow channel being configured as individual portions of a second lumen extending through said sensor;

forming a plurality of alignment holes in penetration through said interrogation layer and disposed with sufficient precision relative to said fifth fluid-flow channel such that installation of two of said alignment holes in registration with respective locating pins of a cooperatingly structured interrogation device is effective to dispose said fifth fluid-flow channel at an interrogation location of said interrogation device within an accuracy of about 50 µm.

14. The method according to claim 13, wherein:
said cassette is structured to interface, at a first orientation, with said interrogation device to permit interrogation of a first fluid sample; and
said cassette is structured to interface, at a second orientation, with said interrogation device to permit interrogation of a second fluid sample.

15. The method according to claim 13, wherein:
said first orientation is 180 degrees rotated from said second orientation.

16. The method according to claim 13, wherein:
alignment holes formed in penetration through said first layer and said third layer are over-size, compared to alignment holes formed in penetration through said interrogation layer, to resist contact between material of said first layer and said third layer and said locating pins.

17. A method for interrogating particles entrained in a carrier fluid, comprising:
a) providing a microfluidic test cassette comprising:
a plurality of stacked thin film substantially planar layers forming a cassette providing structure defining a fluid path disposed inside said sensor, said path comprising:
a first portion disposed parallel to, and within, said layers;
a second portion provided by a tunnel passing through an interrogation layer, a constriction in said tunnel being sized to urge particles entrained in a carrier fluid into substantially single-file travel through a particle interrogation zone; and
a third portion disposed parallel to, and within, said layers, said first portion and said third portion being disposed on opposite sides of said particle interrogation zone;
b) loading a first fluid sample into said cassette;
c) installing said cassette in operable registration, at a first orientation, with an interrogation device;
d) urging flow of said first fluid sample through said cassette while using said interrogation device to interrogate a portion of said first sample;
e) removing said cassette from said interrogation device;
f) loading a second fluid sample into said cassette;
g) re-installing said cassette in operable registration, at a second orientation, with said interrogation device; and
h) urging flow of said second fluid sample through said cassette while using said interrogation device to interrogate a portion of said second sample.

18. A method for interrogating particles entrained in a carrier fluid, comprising:
a) providing a microfluidic test cassette comprising:
a plurality of stacked thin film substantially planar layers forming a cassette providing structure defining a fluid path disposed inside said sensor, said path comprising:
a first portion disposed parallel to, and within, said layers;
a second portion provided by a tunnel passing through an interrogation layer, a constriction in said tunnel being sized to urge particles entrained in a carrier fluid into substantially single-file travel through a particle interrogation zone; and
a third portion disposed parallel to, and within, said layers, said first portion and said third portion being disposed on opposite sides of said particle interrogation zone;
certain of said layers carrying one or more electrode to dispose a plurality of electrodes in a 3-dimensional array in space; said electrodes comprising:
a first stimulated electrode disposed for contact with fluid in said first portion;
a second stimulated electrode disposed for contact with fluid in said third portion; and
a first interrogation electrode disposed for contact with fluid between said first stimulated electrode and said second stimulated electrode;
b) interrogating a plurality of fluid samples in series; and
c) electrically monitoring a health-indicating parameter of said cassette between at least two of said samples.

19. The method according to claim 18, further comprising:
flushing said fluid path with a cleaning fluid during an interval between the interrogation of at least two of said fluid samples.

20. The method according to claim 18, further comprising:
accumulating said fluid samples inside a container carried by said cassette.

* * * * *

UNITED STATES PATENT AND TRADEMARK OFFICE
CERTIFICATE OF CORRECTION

PATENT NO. : 8,616,048 B2  
APPLICATION NO. : 12/985536  
DATED : December 31, 2013  
INVENTOR(S) : Harold E. Ayliffe Page 1 of 1

It is certified that error appears in the above-identified patent and that said Letters Patent is hereby corrected as shown below:

Title Page: Related US Application Data should read:

Item (63)  Continuation-in-part of application No. 12/381,252, filed on Mar. 10, 2009, now Pat. No. 8,171,778, which is a continuation-in-part of application No. 11/800,167, filed on May 4, 2007, now Pat. No. 7,520,164, application No. 12/986,536, which is a continuation-in-part of 12/378,757, filed on Feb. 19, 2009, now Pat no. 8,072,603, which is a continuation-in-part of application No. 11,701,711, filed on Feb. 2, 2007, now Pat. No. 7,515,268, application No. 12/986,536, which is a continuation-in-part of 12/936,243, filed on Oct. 4, 2010, now Pat. No. 8,182,635, which is a 35 USC 371 of PCT/US2009/002172, filed April 7, 2009.

In the Specification

Col 1, first paragraph, lines 5-28 should read:

This application is a continuation-in-part of U.S. utility application Ser. No. 12/381,252, filed Mar. 10, 2009, which is a continuation-in-part of US utility application Ser. No. 11/800,167, filed May 4, 2007, now U.S. utility patent No. 7,520,164, and claims the benefit under 35 U.S.C. 119(e) of the filing date of Provisional Application Ser. No. 60/798,155, filed May 5, 2006, for "THIN FILM PARTICLE SENSOR"; and is a continuation-in-part of U.S. utility application Ser. No. 12/378,757, filed Feb. 19, 2009, which is a continuation-in-part of U.S. utility application Ser. No. 11/701,711, filed Feb. 2, 2007, now U.S. utility patent No. 7,515,268, and claims the benefit under 35 U.S.C. 119(e) of the filing date of Provisional Application Ser. No. 60/764,697, filed Feb. 2, 2006, for "FLUORESCENCE-ACTIVATED CELL DETECTOR"; and is a continuation-in-part of U.S. utility application Ser. No. 12/936,243, filed on Oct. 4, 2010, now Pat. No. 8,182,635, which is a 35 U.S.C. 371 of the International Patent Application filed under the Patent Cooperation Treaty, Serial No. PCT/US2009/002172, and claims the benefit under 35 U.S.C. 119(e) of the filing date of Provisional Application Ser. Nos. 61/123,248, filed April 7, 2008 and 61/124,121, filed April 14, 2008, for "METHOD FOR MANUFACTURING A MICROFLUIDIC SENSOR", the entire disclosures of which are all hereby incorporated by this reference as though set forth in their entirety herein.

Signed and Sealed this  
Fourth Day of November, 2014

Michelle K. Lee  
*Deputy Director of the United States Patent and Trademark Office*